United States Patent
Arcand et al.

(10) Patent No.: US 12,005,130 B2
(45) Date of Patent: Jun. 11, 2024

(54) GENERATING MICROBUBBLES FOR BUBBLE STUDIES

(71) Applicant: Agitated Solutions Inc., Oakdale, MN (US)

(72) Inventors: Benjamin Arcand, Minneapolis, MN (US); Carl Lance Boling, San Jose, CA (US); Morgan Evans, Apple Valley, MN (US); Micah J. Eimer, Glenview, IL (US); Jennifer Chmura, Minneapolis, MN (US)

(73) Assignee: Agitated Solutions Inc., St. Paul, MN (US)

( * ) Notice: Subject to any disclaimer, the term of this patent is extended or adjusted under 35 U.S.C. 154(b) by 748 days.

(21) Appl. No.: 17/071,388

(22) Filed: Oct. 15, 2020

(65) Prior Publication Data

US 2021/0113718 A1 Apr. 22, 2021

Related U.S. Application Data

(60) Provisional application No. 63/026,175, filed on May 18, 2020, provisional application No. 62/915,781, filed on Oct. 16, 2019.

(51) Int. Cl.
*A61K 49/22* (2006.01)
*A61M 5/315* (2006.01)
(Continued)

(52) U.S. Cl.
CPC ....... *A61K 49/223* (2013.01); *A61M 5/31596* (2013.01); *A61M 2005/006* (2013.01);
(Continued)

(58) Field of Classification Search
CPC . A61K 49/223; A61M 5/31596; A61M 5/007; A61M 2005/006; A61M 2005/3128; A61M 2205/33; B01F 23/235
See application file for complete search history.

(56) References Cited

U.S. PATENT DOCUMENTS 4,406,656 A 11/1983 Hattler et al.
4,705,508 A 11/1987 Karnavas et al.
(Continued)

FOREIGN PATENT DOCUMENTS

CN 101032514 A 9/2007
CN 106731840 A 5/2017
(Continued)

OTHER PUBLICATIONS

Acandis, Catheters, retrieved from https://www.acandis.com/catheters-34-en&print_view=1, last visited Jan. 21, 2021, 2 pages.
(Continued)

*Primary Examiner* — Ariana Zimbouski
*Assistant Examiner* — John A Doubrava
(74) *Attorney, Agent, or Firm* — Matthew J. Smyth

(57) ABSTRACT

A method for generating microbubbles may include providing a syringe having a barrel defining an interior volume, a plunger, a tip and a check valve assembly. The check valve assembly may have an inlet port; a check valve that is configured to open when the plunger is drawn back by a user; and a nozzle in fluid communication with the interior volume and, when the check valve is open, in fluid communication with the inlet port. The method may include drawing liquid into the interior volume; removing a seal from the inlet port and drawing gas adjacent the inlet ports into the interior volume to form microbubbles in the liquid already drawn in; coupling the tip to an intravenous line associated with a patient undergoing a bubble study; and depressing the plunger to force the liquid and the formed microbubbles into the intravenous line.

6 Claims, 13 Drawing Sheets

(51) Int. Cl.
  *A61M 5/00* (2006.01)
  *A61M 5/31* (2006.01)
  *A61M 39/02* (2006.01)
(52) U.S. Cl.
  CPC ..... *A61M 5/007* (2013.01); *A61M 2005/3128* (2013.01); *A61M 2039/0235* (2013.01); *A61M 2205/33* (2013.01)

(56) References Cited

U.S. PATENT DOCUMENTS

| | | |
|---|---|---|
| 4,844,882 A | 7/1989 | Widder et al. |
| 4,986,809 A | 1/1991 | Hattler |
| 5,098,376 A | 3/1992 | Berry et al. |
| 5,265,593 A | 11/1993 | Odland |
| 5,271,743 A | 12/1993 | Hattler |
| 5,376,069 A | 12/1994 | Hattler |
| 5,409,688 A | 4/1995 | Quay |
| 5,501,663 A | 3/1996 | Hattler et al. |
| 5,605,673 A | 2/1997 | Schutt et al. |
| 5,686,060 A | 11/1997 | Schneider et al. |
| 5,823,180 A | 10/1998 | Zapol |
| 5,865,789 A | 2/1999 | Hattler |
| 5,938,634 A | 8/1999 | Packard |
| 6,074,359 A | 6/2000 | Keshaviah et al. |
| 6,261,537 B1 | 7/2001 | Klaveness et al. |
| 6,350,249 B1 | 2/2002 | Zicherman |
| 6,450,963 B1 | 9/2002 | Ackerman |
| 6,537,246 B1 | 3/2003 | Unger et al. |
| 6,572,840 B1 | 6/2003 | Toler |
| 8,021,359 B2 | 11/2011 | Auth et al. |
| 8,063,020 B2 | 11/2011 | Simpkins |
| 8,167,280 B2 | 5/2012 | Chomas et al. |
| 8,282,967 B2 | 10/2012 | Schoenfisch et al. |
| 8,260,411 B1 | 11/2012 | Odland et al. |
| 8,367,613 B2 | 2/2013 | Simpkins |
| 8,419,674 B2 | 4/2013 | Cattaneo et al. |
| 8,470,298 B2 | 6/2013 | Uber, III et al. |
| 8,574,309 B2 | 11/2013 | Galea et al. |
| 8,579,880 B2 | 11/2013 | Grady et al. |
| 8,622,911 B2 | 1/2014 | Hossack et al. |
| 8,647,569 B1 | 2/2014 | Federspiel et al. |
| 8,939,436 B2 | 1/2015 | Takase et al. |
| 9,022,974 B2 | 5/2015 | Rinehart et al. |
| 9,061,255 B2 | 6/2015 | Song et al. |
| 9,845,237 B2 | 12/2017 | Tseng et al. |
| 10,058,837 B2 * | 8/2018 | Borden ............... A61K 49/223 |
| 10,124,126 B2 | 11/2018 | Borden et al. |
| 10,335,530 B2 | 7/2019 | Madhani et al. |
| 10,577,554 B2 | 3/2020 | Kheir et al. |
| 10,646,507 B2 | 3/2020 | Poetzschke et al. |
| 2001/0002993 A1 | 6/2001 | Ostensen et al. |
| 2004/0141921 A1 | 7/2004 | Ostensen et al. |
| 2005/0260189 A1 | 11/2005 | Klibanov et al. |
| 2006/0273695 A1 | 12/2006 | Savage |
| 2007/0059247 A1 | 3/2007 | Lindner et al. |
| 2008/0262413 A1 | 10/2008 | Ladizinsky |
| 2008/0319377 A1* | 12/2008 | Keenan ........... B01F 25/31331 604/24 |
| 2010/0016731 A1 | 1/2010 | Eggers et al. |
| 2010/0228122 A1* | 9/2010 | Keenan ............... A61N 5/1007 604/24 |
| 2010/0224191 A1 | 11/2010 | Dixon et al. |
| 2011/0020236 A1 | 1/2011 | Bohmer et al. |
| 2011/0270156 A1* | 11/2011 | Hassan ................ A61P 9/00 604/24 |
| 2012/0226258 A1 | 11/2012 | Otto et al. |
| 2013/0207285 A1 | 8/2013 | Cooke |
| 2014/0010848 A1 | 1/2014 | Kheir et al. |
| 2014/0171795 A1 | 6/2014 | Eggers et al. |
| 2015/0164787 A1 | 6/2015 | Kheir et al. |
| 2016/0067276 A1 | 3/2016 | Polizzotti et al. |
| 2016/0287809 A1* | 10/2016 | Sharma ............. A61M 25/0108 |
| 2018/0116971 A1* | 5/2018 | Tachibana ................. A61B 8/06 |
| 2019/0314567 A1 | 10/2019 | Straube et al. |
| 2019/0269860 A1 | 11/2019 | Bender et al. |

FOREIGN PATENT DOCUMENTS

| | | |
|---|---|---|
| CN | 110279432 A | 9/2019 |
| CN | 110243454 A | 6/2020 |
| DE | 19622184 A1 | 12/1997 |
| DE | 10341221 A1 | 3/2005 |
| EP | 3041495 A1 | 7/2016 |
| IN | 311914 B | 12/2012 |
| JP | H0621538 Y2 | 6/1994 |
| JP | 5470630 B2 | 4/2014 |
| JP | 6653185 B1 | 2/2016 |
| WO | 2002076530 A1 | 3/2002 |
| WO | 2005028002 A1 | 3/2005 |
| WO | 2006066553 A8 | 6/2006 |
| WO | 2008019102 A2 | 2/2008 |
| WO | 2008147050 A1 | 12/2008 |
| WO | 2012108855 A1 | 6/2012 |
| WO | 2019173387 A1 | 9/2019 |
| WO | 2020123791 A1 | 6/2020 |

OTHER PUBLICATIONS

Admedes, Venous Stents, retrieved from https://www.admedes.com/en/ideas, last visited Jan. 21, 2021, 4 pages.
Associated Press, "What tiny air bubbles are teaching doctors about how COVID-19 damages the lungs," LA Times (AP), Aug. 19, 2020, retrieved from https://www.latimes.com/science/story/2020-08-19/tiny-bubbles-lead-scientists-to-new-coronavirus-clue-lung-damage, last visited Jan. 21, 2021, 9 pages.
Bell-Cheddar et al., "Indications and Evaluation for ASD Closure," Cardiac Interventions Today 2011, p. 48-52, retrieved from https://citoday.com/pdfs/CIT1011_structural_cheddar.pdf, last visited Jan. 21, 2021, 5 pages.
Boston Scientific, Biliary Access, https://www.bostonscientific.com/content/dam/bostonscientific/endo/catalog/2018/Biliary-Access.pdf, last visited Jan. 27, 2021, 13 pages.
Cattaneo et al., "Intravascular Blood Oxygenation Using Hollow Fibers in a Disk-Shaped Configuration: Experimental Evaluation of the Relationship Between Porisity and Performance," ASSAIO Journal 2006, p. 180-185., 6 Pages.
CDC, "Facts about Atrioventricular Septal Defect (AVSD)," retrieved from https://www.cdc.gov/ncbddd/heartdefects/avsd.html, last visited Jan. 27, 2021, 3 pages.
Cheng et al., Complications of Joint, Tendon, and Muscle Injections, Tech Reg Anesth Pain Manage. 2007;11(3): 141-47.
Collado et al., "Patent Foreamen Ovale Closure for Stroke Prevention and Other Disorders," JAHA 2018; 7(12).
Cook, EchoTip, retrieved from https://www.cookmedical.com/products/wh_opsd_webds/, last visited Jan. 21, 2021, 4 pages.
Domenech et al., "Effect of SonoVue on the Synovial Membrane in Rabbit Knees," J Ultrasound Med 2011, 30:1241-1246, retrieved from https://onlinelibrary.wiley.com/doi/pdf/10.7863/jum.2011.30.9.1241, last visited Jan. 21, 2021, 6 pages.
Elson et al., "Development of an intravenous oxygenator using microbubbles," 2014 Cairo International Biomedical Engineering Conference, retrieved from https://ieeexplore.ieee.org/document/7020920, last visited Jan. 21, 2021, 2 pages.
Femvue, Femasys, retrieved from http://femvue.com/, last visited Jan. 21, 2021, 4 pages.
Fraisse et al., "Atrial septal defect closure: indications and contraindications," J Thorac Dis 2018; 10(Suppl 24): S2874-S2881, 8 pages.
Fredberg, "Placement of intra-articular injections verified by ultrasonography and injected air as contrast medium," retrieved at https://ard.bmj.com/content/60/5/542.1, last visited Jan. 27, 2021, 7 pages.
Fresenius Medical Care, Novalung, https://fmcna.com/products/critical-care/novalung/, last visited Jan. 21, 2021, 9 pages.
Green, "Nitric Oxide, BCG, and COVID-19's Weakness," Medpage Today, May 10, 2020, retrieved from https://www.medpagetoday.com/infectiousdisease/covid19/86410?xid=nl_popmed_2020-05-14&eun=g386429d0r&utm_source=Sailthru&utm_medium=email

(56) References Cited

OTHER PUBLICATIONS

&utm_campaign=PopMedicineWinner_051420&utm_content=Final&utm_term=NL_Gen_Int_PopMedicine_Active), last visited Jan. 21, 2021, 9 pages.
Hattler et al., "A respiratory gas exchange catheter: In vitro and in vivo tests in large animals," J Thorac and Card Sur 2002, p. 520-530., 11 pages.
Helix2, Double Lumen Needles, retrieved from http://helix2.gr/double-lumen-needles/, last visited Jan. 21, 2021, 2 pages.
Hernandez-Enriquez et al., "Current Indications for Percutaneous Closure of Patent Foramen Ovale," Inter. J of Card. Diseases 2014; 67(8): 603-607.
Hettiarachchi et al., "On-chip generation of microbubbles as a practical technology for manufacturing contrast agents for ultrasonic imaging," Lab Chip 2007, 7(4): 463-468, retrieved from https://www.ncbi.nlm.nih.gov/pmc/articles/PMC2253663/pdf/nihms-26478.pdf, last visited Jan. 21, 2021, 14 pages.
Hu et al., "Microbubble Injection Enhances Inhibition of Low-Intensity Pulsed Ultrasound on Debris-Induced Periprosthetic Osteolysis in Rabbit Model," Ultrasound in Medicine & Biology 2015, 41(1): 177-186, retrieved from https://www.sciencedirect.com/science/article/abs/pii/S0301562914005687, lat visited Jan. 21, 2021, 2 pages.
Huang et al., "Morphometry of the human pulmonary vasculature," The American Psychological Society 1996, 2123-2133, retrieved from https://pdfs.semanticscholar.org/ed0f/258bd8e53b840fb701461cd2b8cf8e83b0e0.pdf?_ga=2.129795084.1468030525.1611250726-820194694.1611250726, last visited Jan. 21, 2021, 11 pages.
IVF Future, Steiner Tan Needle, https://www.ivffuture.com/steiner-tan-needle/, last visited Jan. 21, 2021, 4 pages.
Jauss, M., & Zenette, E., "Detection of right-to-let shunt with ultrasound contrast agent and transcranail Doppler sonography," Cerebrovascular Dis. 2000; 10(6): 490-96, retrieved from https://www.karger.com/Article/Abstract/16119, last visited Jan. 28, 2021, 2 pages.
Khan et al., "Engineering oxygen nanobubbles for effective reversal of hypoxia," Artificial Cells, Nanomedicine, and Biotechnology, 2018, vol. 46, No. S3, S318-S327, retrieved from https://www.tandfonline.com/doi/pdf/10.1080/21691401.2018.1492420?needAccess=true, last visited Jan. 21, 2021, 11 pages.
Kheir, "Building a better bubble: engineering tweaks bring safe IV oxygen delivery closr to reality," Vector, Boston Children's Hospital's science and clinical innovation blog, retrieved from https://vector.childrenshospital.org/2018/02/building-better-oxygen-bubbles/, last visited Jan. 21, 2021, 7 pages.
Kitazato, Double Lumen, retrieved from https://www.kitazato-dibimed.com/oocyte-pick-up-needles/double-lumen/, last visited Jan. 21, 2021, 8 pages.
Kottoor et al., "Cryptognic Stroke: To Close a Patent Foramen Ovale or Not to Close?" J Cent Nerv Syst Dis. 2018, 10: 1-9, retrieved from https://www.ncbi.nlm.nih.gov/pmc/articles/PMC6297885/pdf/10.1177_1179573518819476.pdf, last visited Jan. 21, 2021, 9 pages.
Landzberg et al., "Indications for the closure of patent foramen ovale," Heart 2004; 90(2) 219-224.
Matsuki et al., "Oxygen supersaturated fluid using fine micro/nanobubbles," International Journal of Nanomedicine, 2014; 9:4495-4505, retrieved from https://www.ncbi.nlm.nih.gov/pmc/articles/PMC4181745/, last visited Jan. 27, 2021, 11 pages.
Mersch, "Ventricular Septal Defect," https://www.medicinenet.com/ventricular_septal_defect/article.htm., last visited Jan. 21, 2021, 9 pages.
Mu et al., "Landmark-Guided and Ultrasound-Guided Approaches for Trochanteric Bursa Injection, Anesthesia and Analgesia," 2017; 124(3): 966-971.
Nakaya et al., "Microbubble-enhanced ultrasound exposure promotes uptake of methotrexate into synovial cells and enhanced antiinflammatory effects in the knees of rabbits with antigen-induced arthritis," Arthritis and Rheumatism 2005, 52(8): 2559-2566, retrieved from https://europepmc.org/article/med/16059891, last visited Jan. 21, 2021, 2 pages.
Nall, Rachel, "What is the Valsalva Maneuver?," Medical News Today, Aug. 2, 2018, retrieved from https://www.medicalnewstoday.com/articles/322661, last visited Jan. 28, 2021, 17 pages.
Nonda et al., Advances in cho Imaging Using Contrast Engancement, 1997, 2nd ed., Springer Netherlands, Netherlands.
Oses et al., "Treatment of Isolated Ventricular SeptalDefects in Children: Amplatzer Versus Surgical Closure," J Athorac Sur 2010, 90: 1593-1598, retrieved from https://www.annalsthoracicsurgery.org/article/S0003-4975(10) 01457-8/pdf, last visited Jan. 21, 2021, 6 pages.
Rocket Medical, Rocket Double Lumen Oocyte Aspiration Needles, retrieved from https://sales.rocketmedical.com/rocket-double-lumen-oocyte-aspiration-needles, last visited Jan. 21, 2021, 2 pages.
Sandella et al., "Evidence Based Approach to Shoulder Injections," DE Orthopaedic Symposium, retrieved from https://www.delawareorthopaedicsymposium.org/wp-content/uploads/2018/11/Evidence-Based-Shoulder-Injections.pdf, last visited Jan. 28, 2021, 24 pages.
Sibbitt, Jr. et al., "Does ultrasound guidance improve the outcomes of arthrocentesis and corticosteroid injection of the knee?," Scandinavian Journal of Rheumatology 2011, 41(1):66-72, retrieved from https://www.researchgate.net/publication/51818480_Does_ultrasound_guidance_improve_the_outcomes_of_arthrocentesis_and_corticosteroid_injection_of_the_knee, last visited Jan. 27, 2021, 5 pages.
Singhal et al., "Morphometry of the Human Pulmonary Arterial Tree," Circulation Research 1973, 33: 190-197, retrieved from https://www.ahajournals.org/doi/pdf/10.1161/01.RES.33.2.190, 8 pages.
Toffaletti et al., "Effect of small air bubbles on changes in blood pO2 and blood gas parameters: calculated vs. measured effects," retrieved from https://acutecaretesting.org/en/articles/effect-of-small-air-bubbles-on-changes-in-blood-po2-and-blood-gas-parameters, last visited Jan. 21, 2021, 8 pages.
Vazquez-Portalatin et al., "Accuracy of utlrasound-guided intra-articular injections in guinea pig knees," Bone & Joint Research 2015, 4(1), retrieved from https://online.boneandjoint.org.uk/doi/full/10.1302/2046-3758.41.2000370, last visited Jan. 21, 2021, 11 pages.
Vitrolife, Double Lumen, https://www.vitrolife.com/products/oocyte-retrieval-needles/double-lumen/, last visited Jan. 21, 2021, 5 pages.
Warnes et al., "ACC/AHA 2018 Guidelines for the Management of Adults with Congenital Heart Disease: Executive Summary," Circulation 2008, 118(23): 2395-2451, retrieved from https://www.ahajournals.org/doi/epub/10.1161/CIRCULATIONAHA.108.190811, 57 pages.
Bhadran, V. & Goharzadeh, A., "Monodispersed microbubble production using modified micro-Venturi bubble generator," AIP Advances 10, 095306 (2020).
Fujiwara, A. et al., "Bubble Breakup Phenomena in a Venturi Tube," ASME, 8(2007), 8 pages.
Huang, J. et al., "A review on bubble generation and transportation in Venturi-type bubble generators," Tsinghua University Press 2019, 12, 12 pages.
Lee, C. H. et al.., "Experimental investigation of microbubble generation in the venturi nozzle," International Journal of Heat and Mass Transfer 136, 1127-1138 (2019), 12 pages.
Liew, K.C.S. et al., "Porous Venturi-Orifice Microbubble Generator for Oxygen Sissolution in Water," Processes, 15(2020), 15 pages.
Alung Technologies, "Use of the Hattler Respiratory Assist Catheter in Severe Respiratory Failure," retrieved from https://clinicaltrials.gov/ct2/show/NCT00288964, last visited Jan. 21, 2021, 3 pages.
Alung, "Vent-Avoid Trial," retrieved from https://www.alung.com/healthcare-professionals-us/, last visited Feb. 1, 2021, 2 pages.
Bernard et al., "Agitated Saline Contrast Echocardiography in the Identification of Intra- and Extracardiac Shunts: Connecting the Dots," J of the Amer. Society of Echocardiography 2021, 34(1): 1-12, 12 pages.
Coran et al., "Core needle biopsy of soft tissue tumors, CEUS vs US guided: a pilot study," J Ultrasound 2015, 18: 335-342, 8 pages.
Daniels et al., "Contrast-enhanced ultrasound-guided musculoskeletal biopsies: our experienec and technique," Skeletal Radiology

(56) References Cited

OTHER PUBLICATIONS 2020, retrieved from https://link.springer.com/article/10.1007/s00256-020-03604-8, last visited Feb. 1, 2021, 9 pages.

Fischer et al., "Contrast-enhanced Ultrasound for Musculoskeletal Applications: A World Federation for Ultrasound in Medicine and Biology Position Paper," Ultrasound in Med. & Biol. 2020, 46(6): 1279-1295, 17 pages.

Gekle et al., "Saline Flush Test: Can Bedside Sonography Replace Conventional Radiography for Confirmation of Above-the-Diaphragm Central Venous Catheter Placement," J Ultrasound Med. 2015, 34: 1295-1299, 5 pages.

Gupta et al., "Saline Contrast Echocardiography in the Era of Multimodality Imaging—Importance of "Bubbling It Right"," Echocardiography 2015, 32: 1707-1719, 13 pages.

Horowitz et al., "The FLUSH Study—Flush the Line and Ultrasound the Heart: Ultrasonographic Confirmation of Central Femoral Venous Line Placement," Annals of Emergency Medicine 2014, 63(6): 678-683, 6 pages.

Jellis and Griffin, "Are We Doing Too Many Inpatient Echocardiograms?" J of the Amer College of Cardiology 2016, 67(5), 512-514, 3 pages.

Karuppasamy, "Real-Time Image-Guided Pericardial Drain Placement," American College of Cardiology, retrieved from https://www.acc.org/latest-in-cardiology/articles/2017/07/12/07/04/real-time-image-guided-pericardial-drain-placement, last visited Feb. 1, 2021, 9 pages.

Passos et al., "Agitated Saline Bubble—Enhanced Ultrasound for Assessing Appropriate Position of ?Hemodialysis Central Venous Catheter in Critically Ill Patients," Kidney International Reports 2017, 2: 952-968, 5 pages.

Sonosite, "Ultrasound Reimbursement Informaiton," retrieved from https://www.sonosite.com/sites/default/files/2020%20SonoSite%20-%20Echo%20Guide%20022020.pdf, last visited Feb. 1, 2021, 3 pages.

Takaya et al., "Important of Abdominal Compression Valsalva Maneuver and Microbubble Grading in Contrast Transthoracic Echocardiography for Detecting Patent Forament Ovale," J of Amer Society of Echocardiography 2020, 201-206, 6 pages.

Wilson et al., "Simplified point-of-care ultrasound protocol to confirm central venous catheter placement: A prospective study," World J Emerg Med 2017, 8(1): 25-28, 4 pages.

\* cited by examiner

GENERATING MICROBUBBLES FOR BUBBLE STUDIES

CROSS-REFERENCE TO RELATED APPLICATIONS

This application claims the benefit of U.S. Provisional Application Ser. No. 63/026,175, titled "GENERATING BUBBLES FOR BUBBLE STUDIES," filed on May 18, 2020, and also claims the benefit of U.S. Provisional Application Ser. No. 62/915,781, titled "SYSTEM AND METHOD TO DELIVER AGITATED SALINE SOLUTION," filed on Oct. 16, 2019. This application incorporates the entire contents of the foregoing applications herein by reference.

TECHNICAL FIELD

Various implementations relate generally to generating microbubbles for diagnosis or therapeutic purposes.

BACKGROUND

Echocardiography refers to the use of ultrasound to study the heart. Echocardiography is a widely used diagnostic test in the field of cardiology and can be used in the diagnosis, management, and follow-up of patients with suspected or known heart diseases. The results from an echocardiography test can provide much helpful information, including the size and shape of the heart's components (e.g., internal chamber size quantification), pumping function, and the location and extent of any tissue damage. An echocardiogram can also give physicians other estimates of heart function, such as a calculation of the cardiac output, ejection fraction (the percentage of blood volume of the left ventricle that is pumped out with each contraction), diastolic function (how well the heart relaxes), etc.

Echocardiography is performed in one of two ways. Least invasively, an ultrasound transducer is placed on a patient's chest, and imaging is done through the patient's chest wall, in a transthoracic echocardiogram (TTE). If a higher fidelity image is required, a more invasive transesophageal echocardiogram (TEE) may be performed, in which an ultrasound transducer disposed on a thin tube is placed down the patient's throat and into the esophagus. Because the esophagus is so close to the heart, this procedure can be employed to secure very clear images of heart structures and valves.

During either a TTE or TEE procedure, a contrast agent may be employed to enhance the imaging of the procedure. This contrast agent may be injected into the patient's vein, such that it quickly reaches the chambers of the heart and is detected by ultrasound to give greater definition to structures of the heart. In some procedures, the contrast agent employed is a saline solution comprising tiny air bubbles (e.g., "microbubbles"), and the procedure may be referred to as an agitated saline contrast study or "bubble study."

SUMMARY

Various implementations relate to producing agitated saline solutions having a greater uniformity of microbubble size, in a manner that relies less on the training or skill of an operator who agitates the saline solution to create microbubbles.

DETAILED DESCRIPTION

Figure 1:
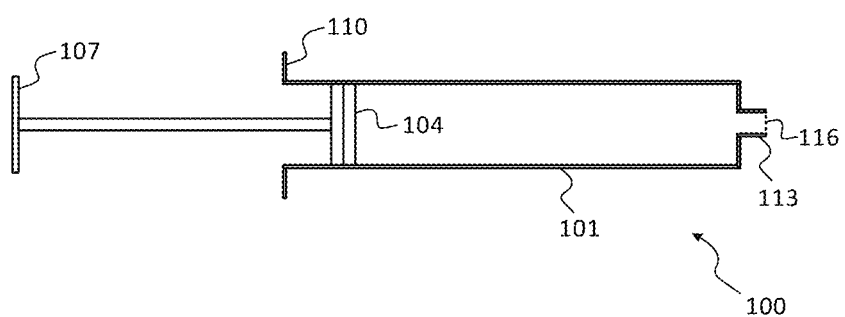
FIG. 1 is a side view of an exemplary syringe.

Agitated saline contrast studies are a useful adjunct to many ultrasound examinations or ultrasound-guided procedures, particularly cardiac ultrasound (echocardiography). Injection of agitated saline into a vein combined with echocardiography is a validated method to detect shunts which may be within the heart such as a patent foramen ovale, (PFO) or an atrial septal defect (ASD)—two types of holes in the heart) or external to the heart (e.g., in the lungs) known as pulmonary arteriovenous malformations (pAVM). Agitated saline can also be used with echocardiography to confirm catheter placement in fluid around the heart (pericardiocentesis), detect anomalous connections within the heart, visualize the right side of the heart and accentuate right sided blood flow for the purpose of quantitation.

Agitated saline contrast echocardiography takes advantage of the increased reflection that results when ultrasound waves meet a liquid/gas interface. This allows for visualization of otherwise poorly reflective areas such as fluid filled cavities by the ultrasound machine. Applications in which this has been clinically useful include echocardiography where agitated saline can be used to define the structural integrity of the interatrial septum or infer the presence of a transpulmonary shunt. Agitated saline can also be combined with Doppler echocardiography to assess blood flow through the tricuspid valve. An alternative method to detect atrial defects uses ultrasound of the brain vessels (transcranial Doppler) to detect microbubbles that have crossed from the right heart to the left heart and entered the cerebral circulation.

At present there is no uniform method to generate agitated saline for these studies which results in varying levels of quality and safety. As a result, current bubble studies have considerable variability in the amount, size, and quantity of microbubbles generated. Such imprecise mixtures of saline and air can result in risk to patients and production of false negative studies. In addition, few individuals may be properly trained to safely perform bubble studies. The productivity of an echocardiography lab may be substantially slowed by this lack of trained personnel; and even trained personnel who do not routinely perform agitated saline studies may be reluctant to do so citing concerns about comfort with the procedure.

Described herein are various methods of agitating saline to produce microbubbles for an ultrasound-based bubble study. The advantages of these approaches include the production of more uniform and consistently dimensioned microbubbles with minimal training. This may result in greater patient safety and comfort as well as studies with improved diagnostic benefit.

Saline is referenced with respect to various implementations. In some implementations, this could be "NSS," or 0.9% normal saline solution; in other implementations, "45 NS," or 0.45% normal saline may be used. In still other implementations, liquids other than saline may be used, such as dextrose in water solution (e.g., "D5W," or 5% dextrose in water; "D10W," or 5% dextrose in water), or other solutions commonly used in intravenous applications at sites that are suitable for particular studies. For example, in some implementations, an intravenous solution may include a small quantity of gelofusine, blood or blood constituents (e.g., to make microbubbles formed therein more opaque to ultrasound).

While many implementations are described with reference to heart studies, agitated contrast studies may have other useful applications. For example, agitated saline combined with ultrasound has also been clinically useful in documentation of proper catheter placement during pericardiocentesis and in central venous catheter placement in the right atrium and during interventional radiology procedures. In the field of gynecologic ultrasound/infertility, agitated saline can be used to assess patency of the fallopian tubes. Agitated saline may also be of use in ultrasound-guided orthopedic procedures. Other applications exist.

In several implementations, a standard syringe design is modified in manners that are described. By way of reference, a standard syringe 100 is illustrated in FIG. 1. As shown, the syringe includes a barrel 101, a plunger 104, a plunger handle 107, a flange 110, and a tip 113. Optionally, the syringe 100 may include a seal 116, which can either protect a sterile state of the interior of the barrel 101 in the case of an empty syringe 100, or it can preserve the sterility of a pre-loaded volume of liquid in the syringe 100 and prevent that liquid from leaking out prior to use of the syringe 100. In some implementations, the tip 113 may include threads or other connections (e.g., a luer lock) to facilitate engagement of the tip with other medical equipment, such as a needle, intravenous tubing, a stop cock, etc.

Figure 2A:
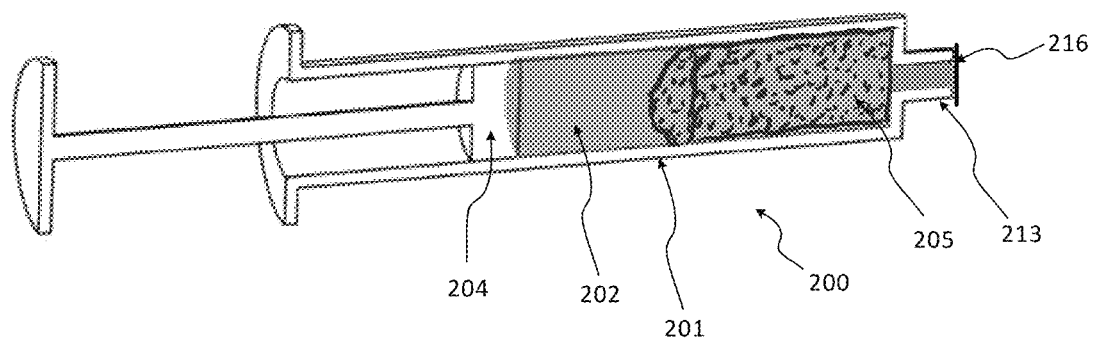
FIG. 2A is a cutaway view of an exemplary syringe with aerated foam.

In one implementation, as shown in FIG. 2A, a syringe 200 may include a liquid 202, such as a saline solution (e.g., "NSS," or 0.9% normal saline solution; "45 NS," or 0.45% normal saline) or a dextrose in water solution (e.g., "D5W," or 5% dextrose in water), and a foam material 205 that has been disposed at the end of the syringe 200. In some implementations, the liquid 202 is drawn into the syringe 200 immediately prior to the syringe 200 being used to generate and inject microbubbles into a patient.

The foam material 205 may comprise a closed-cell or partially-closed-cell biocompatible foam; alternatively, the foam material 205 may comprised an open-cell biocompatible foam, such as an elastomeric foam. In any case, air may be trapped within the foam material 205, such that, upon compression (e.g., by depression of the plunger 204), air that is trapped in the foam material 205 is released into the liquid 202 as the liquid 202 is ejected from the syringe 200, into, for example, intravenous tubing that is disposed in the vein of a patient undergoing a bubble study. The air may be released in the form of microbubbles, and the size of the microbubbles may be determined by the nature of the pockets within the foam material 205 that trap the air in the first place.

In some implementations, the foam material 205 may be an elastomeric polymer that is biocompatible, and the foam material 205 may be produced from a hydrogel via desiccation, freeze drying (e.g., lyophilizing) or supercritical drying. The foam may be disposed in a distal portion of the barrel 201, towards the tip 213.

Figure 2B:
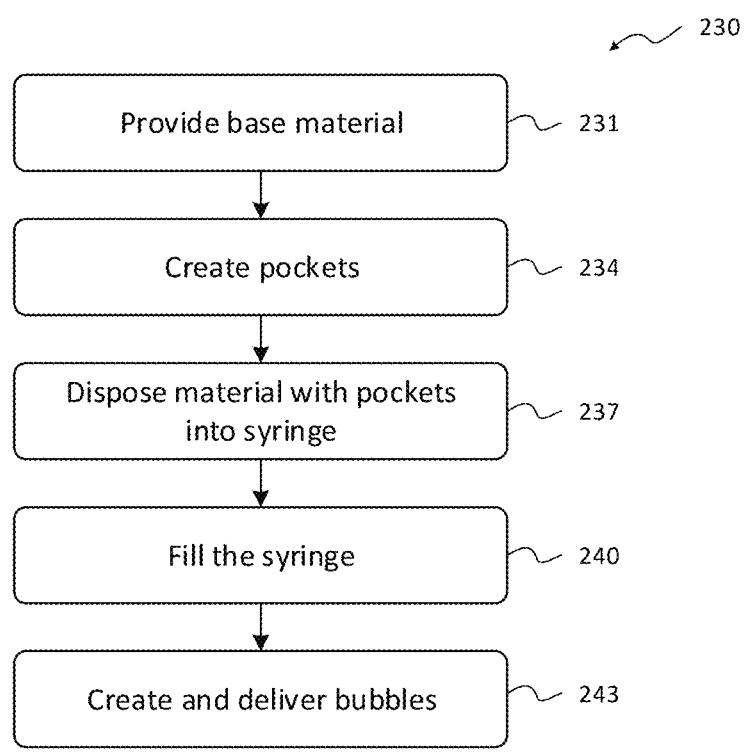
FIG. 2B is a flow diagram of an exemplary method for creating and delivering microbubbles.

FIG. 2B illustrates an exemplary method 230. As shown, the method 230 comprises providing (231) a base material, such as a base material that ultimately comprises the foam material 205. For example, in one implementation, a biocompatible elastomeric polymer may be provided; as another example, in another implementation, a hydrogel may be provided.

The method 230 further comprises creating (234) air pockets in the base material. In some implementations, this could include providing in the elastomeric polymer, spheres of substantially uniform size (e.g., having a size distribution of, for example, 95% having a diameter within a particular range, such as within 10% of an average diameter; or, as another example 68% within 20% of average diameter). In some implementations, the spheres remain intact during a process of forming the elastomer but that can be crushed upon application of pressure on the final elastomeric polymer. For example, such spheres could comprise a polymer coating over a quantity of biocompatible gas (e.g., oxygen, carbon dioxide, nitrogen, or some combination thereof).

In some implementations, the method 230 comprises creating (234) pockets in a hydrogel by, for example, freeze drying (e.g., lyophilizing), super-critically drying or desiccating the hydrogel in a manner that results in pockets of air forming with substantially similar volumes.

The method 230 further includes disposing (237) the material with pockets (e.g., the base material provided (231) in which pockets were created (234), such as the foam material 205) into the syringe. In some implementations, disposing (237) the material, such as foam material 205, into the syringe 200 comprises removing the plunger 204, sliding foam material 205 that is shaped to conform to the interior of the barrel 201, reinstalling the plunger 204, and depressing the plunger 204 until it pushes the foam material 205 as close to the tip 213 as possible without crushing the foam material 205 too substantially.

The method 230 further includes filling (240) the syringe with a liquid, such as, for example, saline or a water and dextrose combination. In such implementations, a seal 216 may first be removed from the tip 213, and the syringe 200 may be coupled to other medical equipment (not shown), such as intravenous tubing disposed in a patient undergoing a bubble study. In other implementations, the syringe 200 may be prefilled, and the seal 216 may be removed immediately prior to use.

The method 230 further includes creating and delivering (243) microbubbles. For example, the plunger 204 may be depressed, causing the foam material 205 to be crushed, releasing trapped air and creating microbubbles that are combined with the liquid 202 as it is expelled from the syringe 200 and delivered.

Figure 2C:
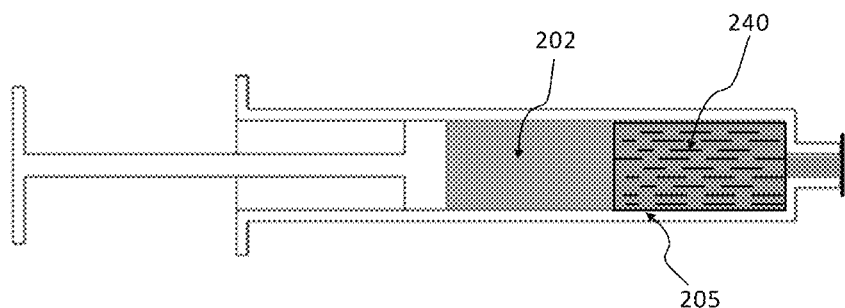
FIG. 2C is a cutaway view of another exemplary syringe with aerated foam.

In some implementations, such as shown in FIG. 2C, the foam material 205 may include cavities or channels 240 to increase surface area and to create turbulence in the prefilled liquid 202 as it is expelled from the syringe 200.

In some implementations, the foam material 205 may be integrated into the wall of the syringe, such that as the plunger 204 is depressed, the foam material 205 is crushed, emitting gas into the pre-filled liquid 202 in the form of microbubbles. Alternatively, foam may be added to the end of the syringe (e.g., integrated in medical tubing between the syringe and a patient undergoing a bubble study). In some implementations, the foam is a mesh foam. In some implementations, the foam may occupy substantially all of the interior of the barrel of the syringe. In some implementations, the foam may be disposed circumferentially, on an interior surface of the barrel 201 of the syringe 200.

Figure 3A:
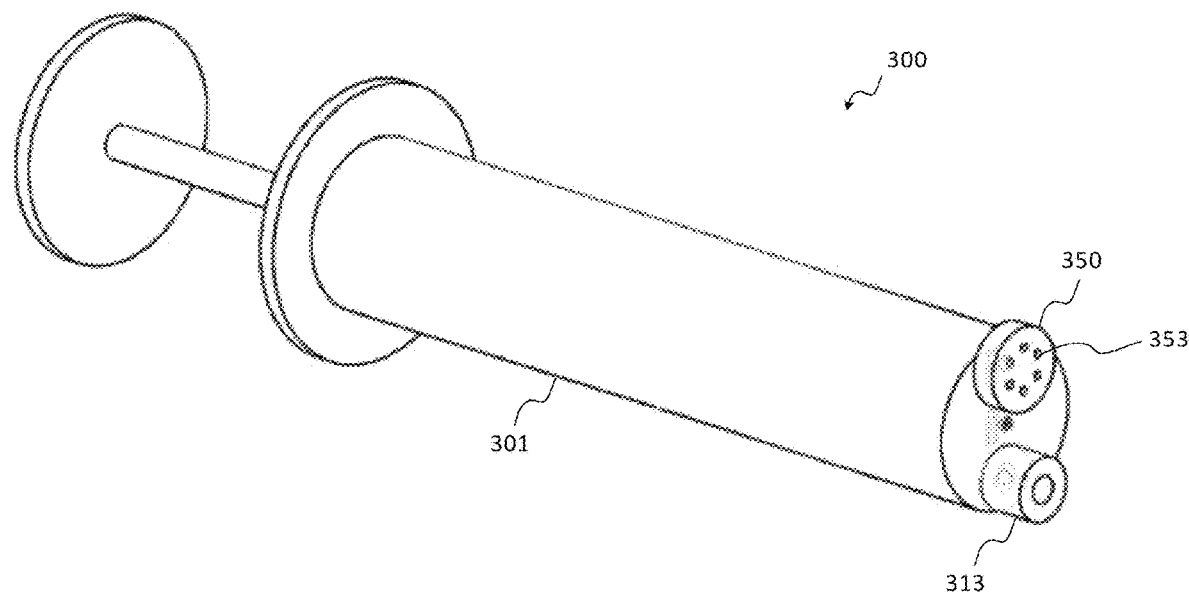
FIG. 3A is a perspective view of an exemplary syringe having a check valve assembly.
Figure 3B:
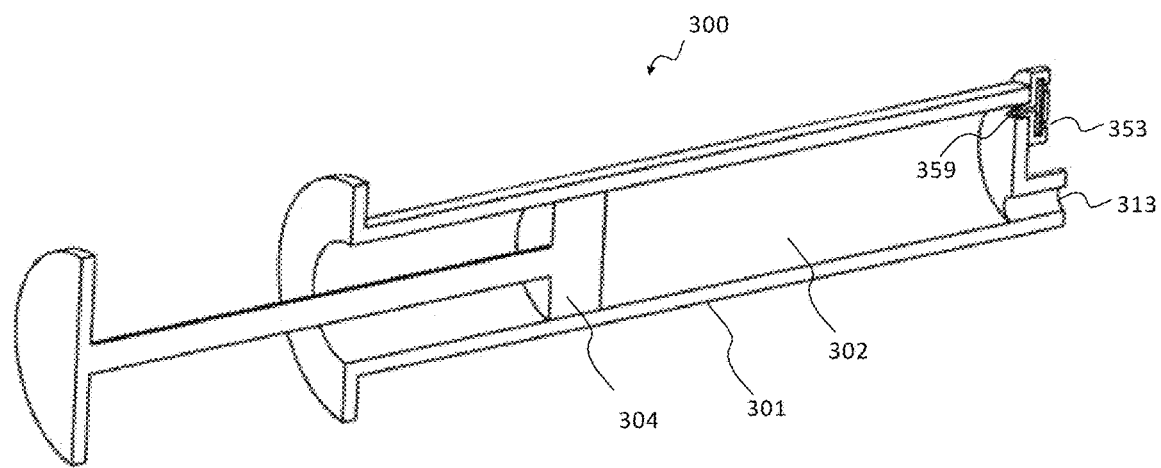
FIG. 3B is a cutaway view of the syringe of FIG. 3A.
Figure 3C:
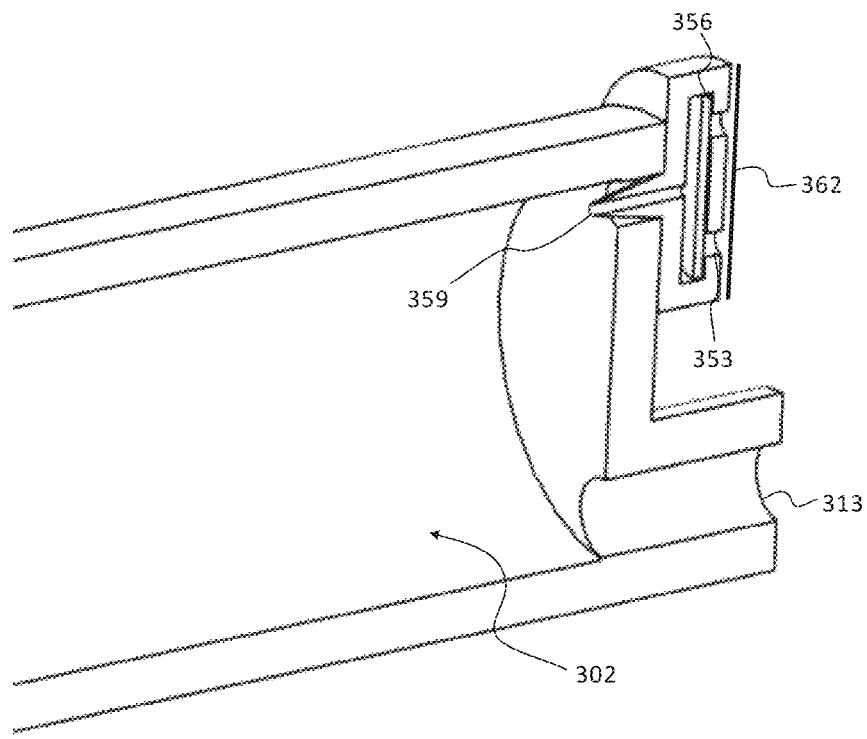
FIG. 3C is another cutaway view of the syringe of FIG. 3A.

In one implementation, as shown in FIGS. 3A, 3B and 3C, a syringe 300 comprises a barrel 301 having an interior volume 302, a tip 313, and a check valve assembly 350. The check valve assembly 350 comprises one or more inlet ports 353, a check valve 356, and one or more nozzles 359.

The check valve 356 is configured to open (e.g., fluidly couple the interior volume 302 to the exterior of the syringe 300, via the one or more inlet ports 353 and the one or more nozzles 359) when the plunger 304 is drawn back. The check valve 356 may be a flexible (e.g., rubber or silicone) membrane that is anchored to a part of the housing of the check valve assembly 350, such that it opens inward, towards the interior volume 302. In some implementations, a removable seal 362 is provided to seal off the one or more inlet ports 353.

Figure 3D:
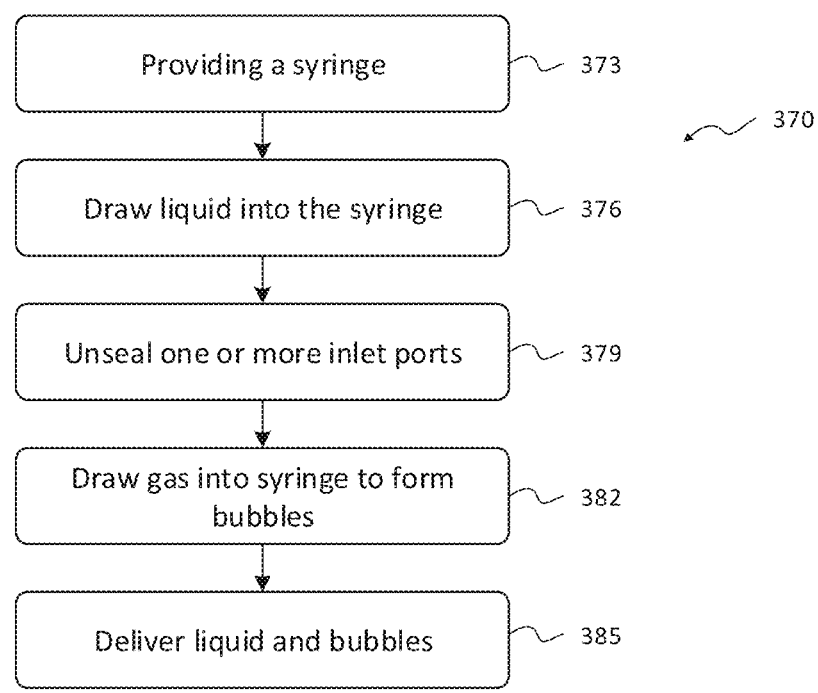
FIG. 3D is a flow diagram of an exemplary method for creating and delivering microbubbles.

In operation, in some implementations, as depicted in FIG. 3D, a method 370 comprises providing (373) a syringe (e.g., a syringe 300 having an interior volume 302, a tip 313 and a check valve assembly 350; the syringe 300 may also have a removable seal 362 that initially blocks the one or more inlet ports 353 from being in fluid communication with a space exterior to the syringe 300). The method 370 further comprises drawing (376) liquid into the syringe. For example, the tip 313 of the syringe 300 can be coupled to a liquid source, such as an intravenous bag containing saline; and the plunger 304 can be drawn back by a user to draw the saline into the interior volume 302. In some implementations, the plunger may not be fully drawn back; rather, some space may be left, such that the plunger 304 can be further drawn back to pull in a gas (e.g., air) in a subsequent step.

The method 370 further comprises unsealing (379) the one or more inlet ports. For example, the seal 362 may be removed. In some implementations, the syringe 300 may be decoupled from the liquid source (e.g., a source of intravenous saline solution), and the tip 313 may be sealed.

The method 370 further comprises drawing (382) gas into the syringe to form microbubbles. For example, a user may further retract the plunger (304) to draw gas adjacent the one or more inlet ports 353 (e.g., air), past the check valve 356, through the one or more nozzles 359, into the interior volume 302 of saline or other liquid, forming microbubbles.

A diameter of the one or more nozzles 359 may correspond to a desired diameter of microbubbles to be formed; that is, the microbubbles formed may have a diameter that is, in some implementations, within 10%, 20%, 50%, 100%, 200%, 400%, 1000%, 2000%, 4000%, etc. of a diameter of the one or more nozzles 359 (e.g., the bubble size may be a multiple of the nozzle diameter size), and thus, a diameter of the one or more nozzles 359 may be selected to engineer the desired size. More particularly, if, in a specific implementation, bubbles are formed that are, on average, 400% of the diameter of the diameter of the one or more nozzles 359; and if the desired microbubble size is 4 microns; then the diameter of the one or more nozzles 359 may be configured to be 1 micron. In some implementations, the diameter of the one or more nozzles 359 may be about (e.g., within 0.1%, 1%, 2%, 5%, 10%, 20%, 25%, 50%) 500 angstroms, 1 micron, 2 microns, 3 microns, 4 microns, or between 5 microns and 10 microns.

The method 370 further comprises delivering (385) liquid and microbubbles. For example, a user may couple the tip 313 of the syringe 300 to an intravenous line that is coupled to a patient undergoing a bubble study (and unseal that tip 313 first, if it was sealed in a previous step); the user may then depress the plunger 304, forcing the liquid (e.g., saline) and microbubbles into the intravenous line. During this portion of the method 370, the check valve 356, by its design, may seal off the one or more inlet ports 353, preventing any escape of liquid or air through the check valve assembly 350.

In some implementations, other steps may be included in the method 370; steps may be reordered; or steps may be omitted.

Figure 4A:
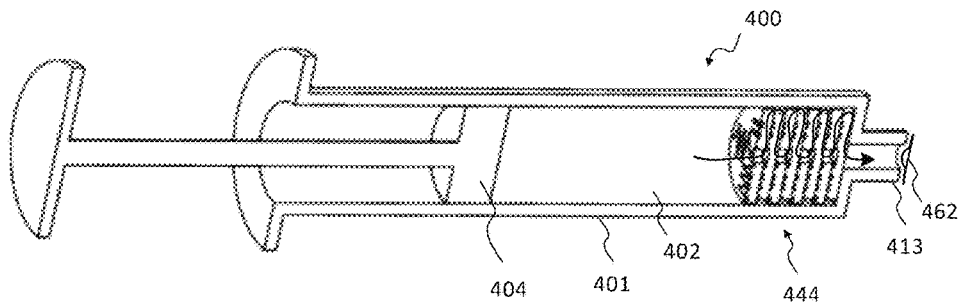
FIG. 4A is a cutaway view of a syringe having microfluid discs.

In some implementations, as shown in FIG. 4A, a syringe 400 comprises a barrel 401, a plunger 404, a tip 413, and a seal 462 for the tip. The barrel 401 defines an interior volume 402, which, in some implementations, is prefilled with saline or another solution. The syringe 400 further comprises a series of microfluid discs 444.

Figure 4B:
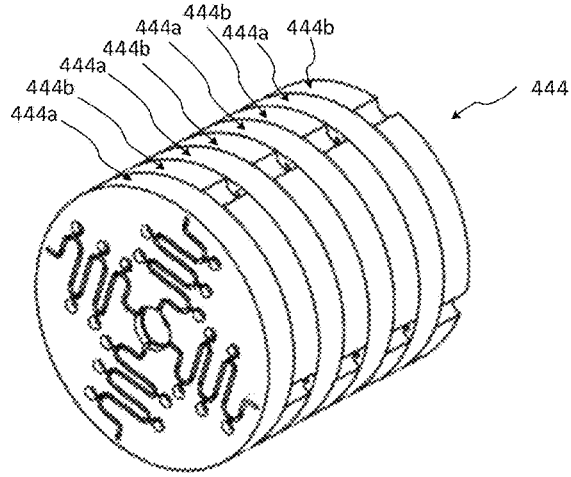
FIG. 4B is a perspective view of a stack of microfluid discs.

As shown in FIG. 4B, the microfluid discs 444 comprise outward-flowing discs 444a and inward-flowing discs 444b. The discs are stacked and alternate between inward-flowing discs 444a and outward-flowing discs 444b.

Figure 4D:
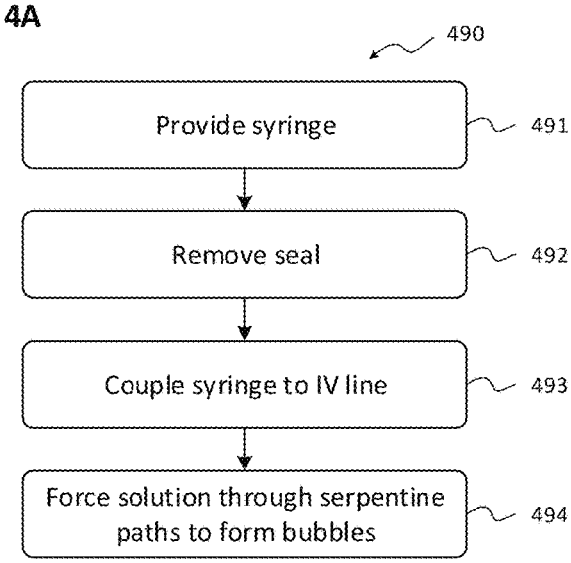
FIG. 4D is a flow diagram of an exemplary method for forming microbubbles.
Figure 4C:
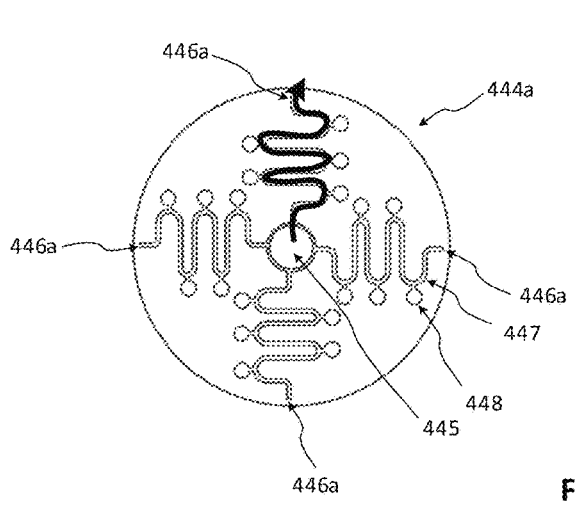
FIG. 4C illustrates detail of inward-flowing and outward-flowing microfluid discs.
Figure 4C:
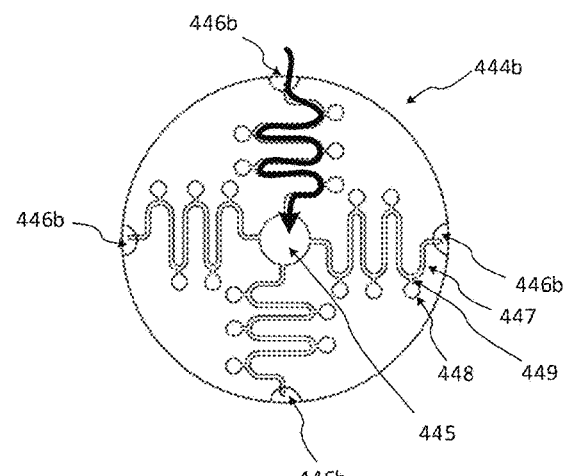

As shown in FIG. 4C, each disc 444a or 444b comprises a central channel 445 and a plurality of outer channels 446a or 446b. Serpentine paths 447 couple the central channel 445 in each of the discs 444a and 444b to the outer channels 446a or 446b. The microfluid discs 444 are configured such that, in an outward-flowing disc 444a, fluid can flow from the central channel 445 to the outer channels 446a, via serpentine paths 447, in the direction depicted by the arrow; and in an inward-flowing disc 444b, fluid can flow from the outer channels 446b to the central channel 445 via the serpentine paths 447, in the direction depicted by the arrow.

Multiple cavities 448 are disposed along the serpentine paths 447, and each cavity 448 is fluidly coupled to its corresponding serpentine path 447 at an orifice 449. In some implementations, the serpentine paths 447, at least near each orifice 449, is configured to be hydrophobic. Moreover, in some implementations, orifices 449 are configured to resist ingress of solutions (e.g., saline or water) in the serpentine paths 447 (e.g., by being dimensioned in such a way that a surface tension of the solution resists such ingress). In such implementations, even if the serpentine paths 447 are filled with a solution, the cavities 448 may remain free of the solution (e.g., they may trap air pockets). In use, when solution in the barrel 401 of the syringe 400 is forced out through the serpentine paths 447, a vacuum force may develop as solution is expelled past the cavities 448, causing air previously trapped in such cavities 448 to be extracted and introduced into the solution as microbubbles.

In some implementations, size of the microbubbles generated may correspond to a size or volume of the cavities 448. In some implementations, size of the microbubbles may depend on the hydrophobicity or hydrophilicity of the serpentine paths 447 near the orifices 449. In some implementations, size of the microbubbles may depend on a corresponding size of the orifices 449. Accordingly, size of microbubbles generated may be controlled in some implementations by design choices associated with the microfluid discs 444.

The microfluid discs 444 may be manufactured in multiple ways. For example, the discs could be laser etched from a heterogenous material with regions that are hydrophobic and other regions that are hydrophilic. The regions could be arranged in a manner that achieves desired results for hydrophobicity or hydrophilicity of serpentine paths relative to air cavities. Discs could be chemically etched from similar material in a process that is akin to semiconductor or printed circuit board manufacturing. Discs could be 3D-printed. Discs could be molded. Discs could comprise elastomeric materials. Discs may be manufactured via soft lithography.

Paths may be spiral in shape, rather than serpentine; or they may take other shapes. Ridges may take the place of cavities or may supplement cavities. In implementations involving spiral paths with ridges, ridges along the path may "filter out" bubbles having particular sizes as liquid is forced along the spiral path (e.g., via a cyclone effect that creates centrifugal forces on the bubbles in the fluid). In other implementations, ridges may create turbulence that acts differently on bubbles of different sizes, thereby facilitating a filtering effect. In some implementations, ridges or other physical features may create turbulence that itself creates microbubbles.

Returning to FIG. 4B, the discs 444 alternate between outward-flowing discs 444a and inward-flowing discs 444b, such that fluid can be routed along serpentine paths 447 radially outward and radially inward through the stack 444 (as depicted by the arrow in FIG. 4A).

FIG. 4D depicts an exemplary method 490 for creating microbubbles. The method 490 includes providing (491) a syringe, such as the syringe 400 shown in FIG. 4A and having microfluid discs 444a and 444b and being pre-filled with, for example, saline. (In some implementations, the syringe is not pre-filled with liquid.)

The method 490 comprises removing (492) a seal on the tip of the syringe. For example, the seal 462 may be removed (492) from the tip 413. In some implementations, the seal 462 is provided to maintain sterility of solution in the interior volume 402 of the syringe 400 (e.g., saline), prior to use of the syringe.

The method 490 comprises coupling (493) the syringe to an IV line, such as an IV line disposed in a patient undergoing a bubble study.

The method 490 further comprises forcing (494) solution (e.g., saline) through the serpentine paths to form microbubbles. For example, a user may depress the plunger 404 to force saline in the interior volume 402 to be forced through the serpentine paths 447, past cavities 448 containing air. A vacuum force may develop as the solution is forced along the serpentine paths 447, such that air is extracted from the cavities 448 in the form of microbubbles.

Figure 5A:
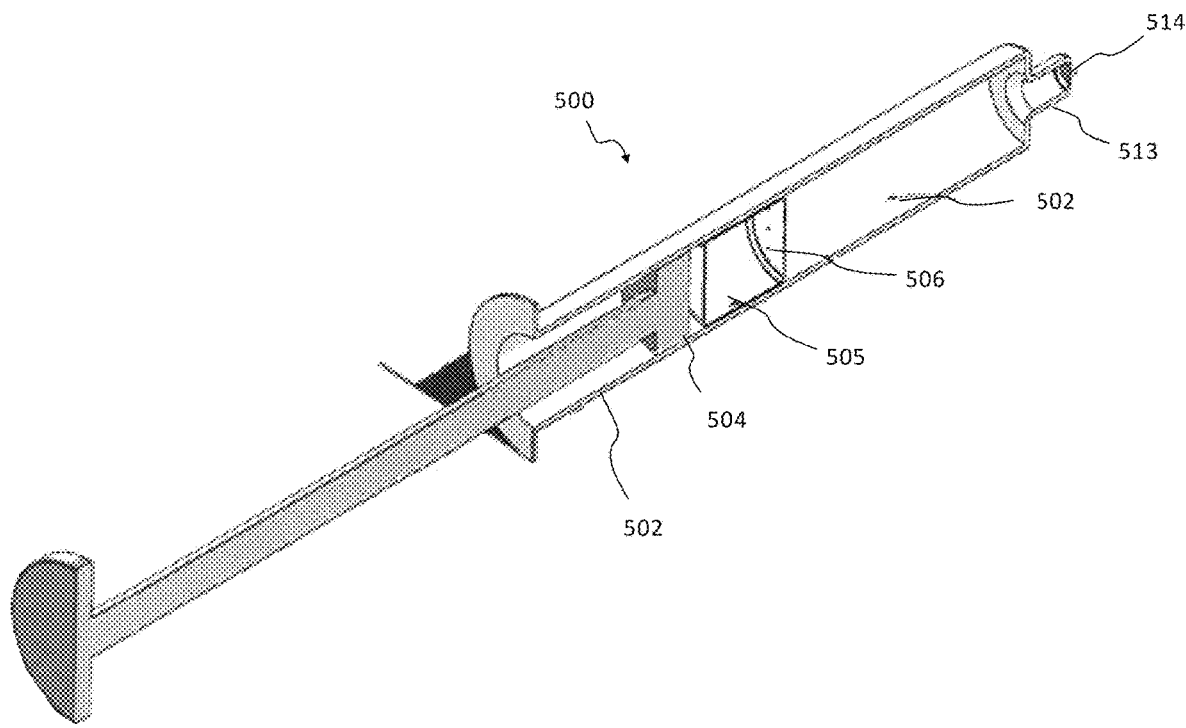
FIG. 5A is a cutaway view of an exemplary syringe with a gas reservoir.

In some implementations, as shown in FIG. 5A, a syringe 500 includes a housing 502, a plunger 504, a tip 513, a pressure cap 514 on the tip 513, an interior volume 502, and a gas reservoir 505 having apertures 506 that fluidly couple an interior of the gas reservoir 505 with the interior volume 502.

The apertures 506 may be sized such that pressure inside the reservoir 505 can be balanced against pressure of the liquid in the interior volume 502. That is, liquid may be disposed inside the interior volume 502 under pressure, and held under such pressure by the pressure cap 514, such that the liquid is kept out of the reservoir 505 by the pressure of a gas inside that reservoir 505, and the gas inside the reservoir 505 is kept out of the liquid in the interior volume 502 by that same balance of pressure.

In some implementations, when this pressure balance is disturbed—for example, through slight withdrawal of the plunger 504, thereby releasing some pressure of liquid in the interior volume 502—gas inside the reservoir 505 escapes into the liquid in the interior volume, thereby creating microbubbles.

In other implementations, compressed gas may be injected from an external gas cartridge attached to the syringe and in communication with a fluid reservoir. The gas (e.g., carbon dioxide) in such an implementation could be actuated by either a manual (via mechanical linkage) or electronically actuated valve. The gas could be in the form of air, carbon dioxide, or any other bio-compatible gas that safely dissipates in human bodies. In another implementation, the gas container may be pre-molded into the syringe body or plunger. As with the gas reservoir 505 shown in FIG. 5A, the pressure from the fluid can restrain the gas pressure; as the fluid pressure decreases (e.g., through withdrawal of the plunger), the gas is released. In another implementation, the gas cylinder may be attached to the end of the syringe, and gas is mixed into the fluid as the fluid is injected.

Figure 5B:
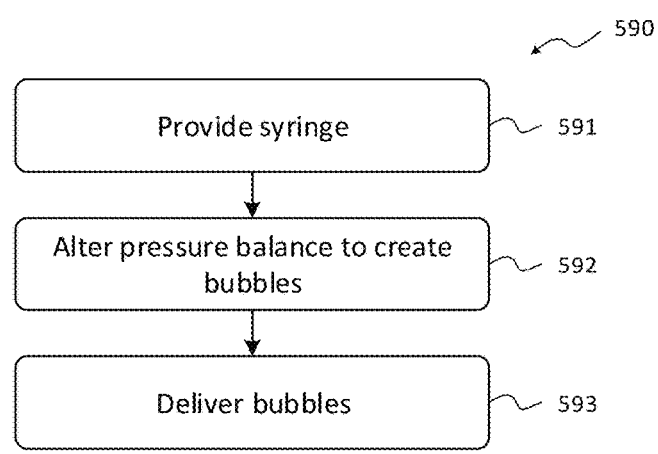
FIG. 5B is a flow diagram of an exemplary method for creating and delivering microbubbles.

FIG. 5B is a flow diagram of an exemplary method 590. The method 590 includes providing (591) a syringe. For example, a syringe 500 could be provided (591), which syringe 500 includes a reservoir 505 containing a pressurized gas and apertures 506; where the syringe 500 includes a liquid (e.g., saline or a dextrose/water combination) that is also under pressure and held that way by a pressure cap 514 and a plunger 504 that is locked into position.

The method 590 includes altering (592) the pressure balance to create microbubbles. For example, a user of the syringe 500 could withdraw the plunger 504, thereby lowering the pressure of liquid in the interior volume 502, and allowing the now-higher pressure gas inside the reservoir 505 to escape through the apertures 506, thereby creating microbubbles in the liquid. Size of the microbubbles may be determined or influenced by dimensions of the apertures, or pressures or relative pressures of liquid in the interior volume 502 or gas in the reservoir 505.

In some implementations, the syringe 500 is provided (591) with the plunger 504 temporarily locked in place. For example, a detent may be provided (not shown) that catches the plunger and prevents its backward movement. To release the plunger 504 from such a detent, a user may twist the plunger 504, prior to withdrawing it. Other mechanisms are possible to lock the plunger 504 in place prior to use or to otherwise maintain a balance of pressures between liquid in the interior volume 502 and gas in the reservoir 505.

The method 590 includes delivering (593) the microbubbles. For example, the tip 513 may be attached to an intravenous line (e.g., through a luer connector) associated a patient undergoing a bubble study. A user may depress the plunger 504, again increasing pressure in the interior volume 502 an causing the pressure cap 514 to release, allowing liquid and microbubbles to be dispensed into the intravenous line.

Figure 6A:
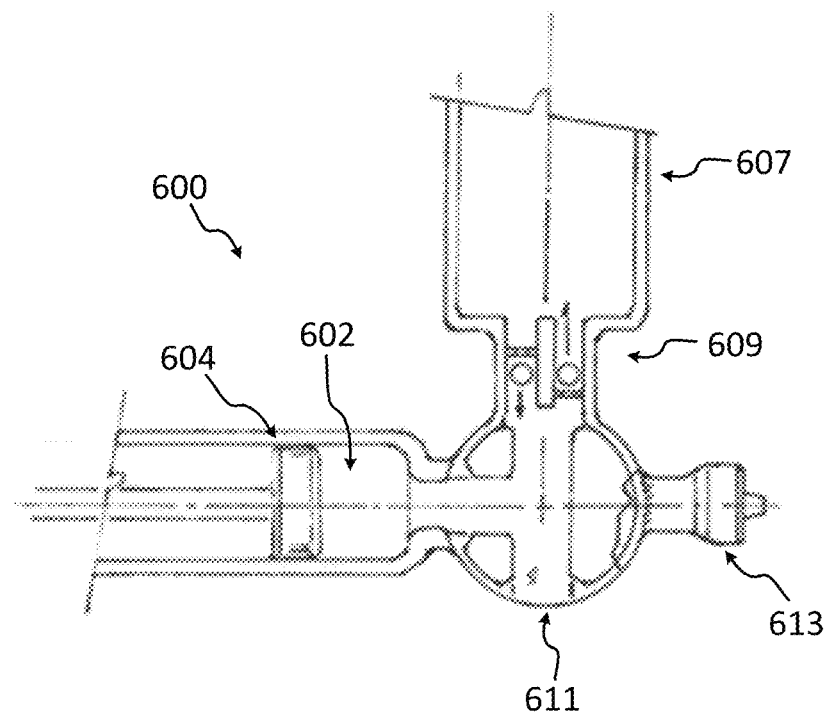
FIG. 6A is a cutaway view of an exemplary shuttle valve mixing syringe.

In some implementations, as shown in FIG. 6A, a syringe 600 includes a syringe reservoir 602 with a plunger assembly 604, an exchange chamber 607, two unidirectional check valves (shuttle valve 609), a circular diverter valve 611, and a distal luer connector 613. The circular diverter valve 611 may be configured to fluidly couple the luer connector 613 to the syringe reservoir 602 when the circular diverter valve 611 is turned one way; and fluidly couple the syringe reservoir 602 to the exchange chamber 607, via the shuttle valve 609, when the circular valve 611 is turned another way (e.g., 90 degrees relative to the first position).

In operation, a user may (a) draw liquid into the syringe 600 with the diverter valve 611 oriented such the luer 613 and syringe body are on axis; (b) once the syringe 600 is filled with liquid, rotate the diverter valve 611 such that the syringe chamber 602 and the exchange chamber 607 are in fluid communication; (c) reciprocate the syringe plunger 604 in and out, circulating the liquid through the shuttle valve 609 and into the exchange chamber, creating microbubbles in the liquid, and continuing agitating to achieve the desired microbubble consistency; and (d) reorient the diverter valve 611 to direct the microbubble filled liquid out through the luer fitting 613 to a patient line (e.g., an intravenous line associated with a patient undergoing a bubble study).

Other implementations could include handle configurations that require only one hand to reciprocate the plunger assembly or embodiments that automatically rotate the diverter valve assembly. In some implementations, turning the diverter valve 611 to different angles may modulate apertures (e.g., in the diverter valve 611 itself) in a manner that influences microbubble size. In some implementations, the diverter valve 611 may be actuated laterally, rather than rotated. For example, pushing the valve in, perpendicular to the flow path, may facilitate fluid communication between the syringe reservoir 602 and the exchange chamber 607; whereas disposing the valve 611 laterally in the opposite direction may facilitate liquid communication between the syringe reservoir 602 and the connector 613 (and any line connected thereto). In some implementations, microbubble size and quantity are determined by how many reciprocations a user executes of the plunger 604 and how many circuits through the shuttle valve 609 the liquid makes.

In some implementations, the exchange chamber may be a flexible bellows structure 607A that is initially filled with air. In operation, a user may, with the diverter valve 611 in a position that enables fluid communication between the interior of the exchange chamber 607A and an interior of the syringe 600, withdraw the plunger 604, until a portion of the air in the flexible bellows 607A has been drawn into the syringe 600. The flexible bellows 607A may provide the user with a visual indication of an amount of air that has been drawn into the syringe 600. For example, the user may withdraw the plunger 604 until the flexible bellows 607A has been compressed to half or one-quarter of its original size.

The user may then actuate the diverter valve 611 to enable fluid communication between the interior of the syringe 600 and a line 615 coupled to the distal luer connector 613, which may, for example, be coupled to a source of saline. By continuing to withdraw the plunger 604, the user may draw in saline from the saline source.

Upon actuation again of the diverter valve 611 to again enable fluid communication between the interior of the syringe 600 and the interior of the flexible bellows 607A, the user may alternately depress and withdraw the plunger 604 to force air and saline back and forth, through the diverter valve 611, between the interior of the syringe 600 and the interior of the flexible bellows 607A. In this manner, microbubbles may be produced (e.g., through cavitation). The expansion and contraction of the flexible bellows 607A may provide the user with a visual indication of progress and visual feedback regarding how far to withdraw or depress the plunger 604. When a sufficient quantity of microbubbles has been generated, the diverter valve 611 may be again actuated to enable fluid communication between the interior of the syringe 600 and the line 615. The line 615 may be then coupled to a patient undergoing a bubble study, and the study may be commenced by injecting the saline with microbubbles into the patient.

Figure 7:
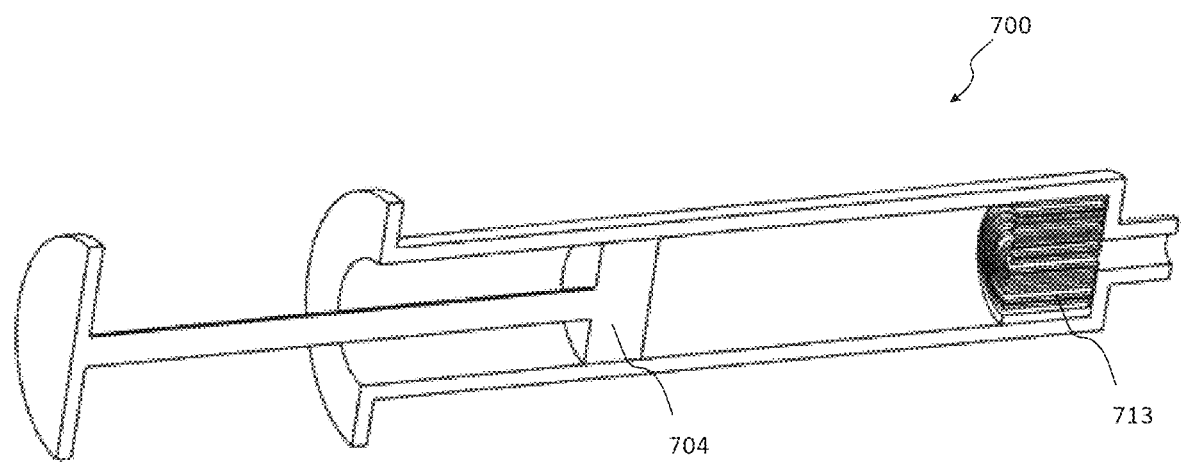
FIG. 7 illustrates an implementation for creating microbubbles with chemical reactions.

FIG. 7 illustrates an implementation in which microbubbles can be created via a chemical reactions. As shown, a rolled paper (or other substrate) cartridge 713 or other porous medium cartridge is impregnated or coated with a chemical that reacts with saline/dextrose solution/blood components drawn into syringe. The reaction may release gas forming small microbubbles on the surfaces of the cartridge that are pushed out of the syringe with the fluid when the plunger 704 is depressed.

In other implementations, gas may be generated as a component of a dissolvable pellet such as example, effervescent antacid tablets made from aspirin, citric acid and sodium bicarbonate. When sodium bicarbonate dissolves in water, it reacts with hydrogen ions from the citric acid and forms carbon dioxide. Because carbon dioxide is a gas, it forms microbubbles inside the water that can are dispersed within the water. In an alternate implementation, a cathodic/anodic reaction may occur to produce microbubble structures.

In other implementations, a dry alkaline base and acidic substance may be applied to the surface of a filter paper or similar substrate and rolled into a loose-fitting scroll and inserted into the syringe. When the scroll is exposed to a fluid, the two components may combine and react, creating microbubbles which can be dispensed within the syringe body and ultimately injected into the vascular system of, for example, a patient undergoing a bubble study.

In still other implementations, an interior wall of a syringe 700 may be coated with a substance capable of producing microbubbles in the presence of water or saline. In some implementations, such a substance may be disposed on the plunger 704 (e.g., a distal portion that is in contact with liquid on an interior of the syringe 700).

In some implementations, an enzyme may be added with the bubble-producing substance (e.g., on a rolled-paper insert, on the interior wall of the syringe 700, on the plunger 704, etc.) to, for example cause a color change in the presence of blood or blood constituents. In such implementations, the color change may provide feedback to a user that the overall system is properly configured (e.g., by detecting a small quantity of blood in the line, confirming a solid venous connection).

Figure 8A:
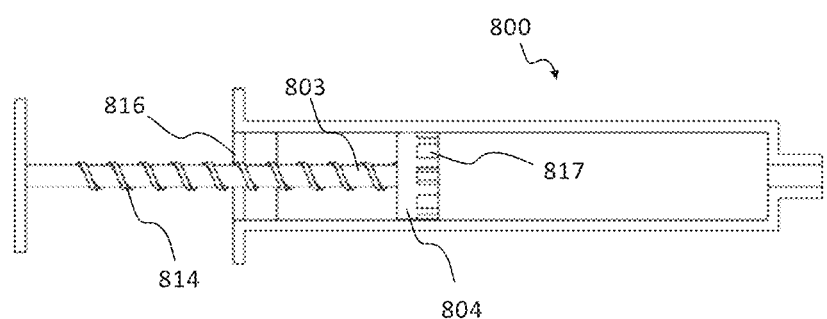
FIGS. 8A and 8B illustrate an exemplary syringe with a screw/nut plunger assembly.
Figure 8B:
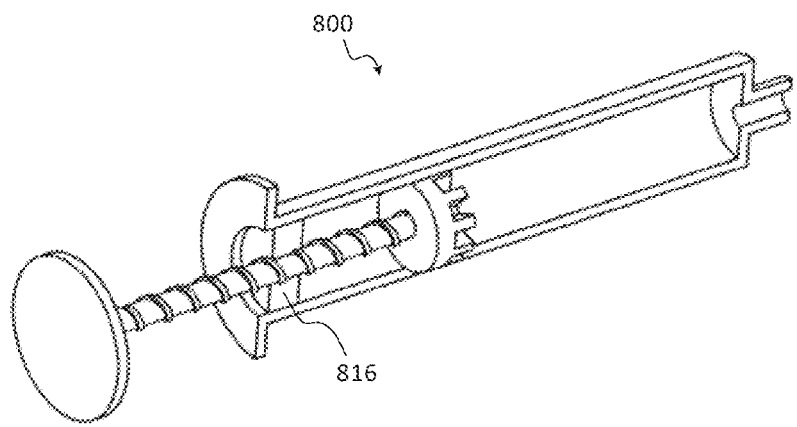

As shown in FIG. 8A and FIG. 8B, a screw/nut assembly (814/816) on the stem 803 of the plunger mechanism 804 causes vanes 817 on the end of the plunger 814 to rotate. With a syringe partially filled with fluid, drawing air in by pulling back on the plunger causes the vanes 817 to spin, mixing the air and fluid in the syringe 800. Mechanisms such as gearing may be used to change the speed of the vane rotation relative to the plunger draw to facilitate better mixing conditions.

Figure 8C:
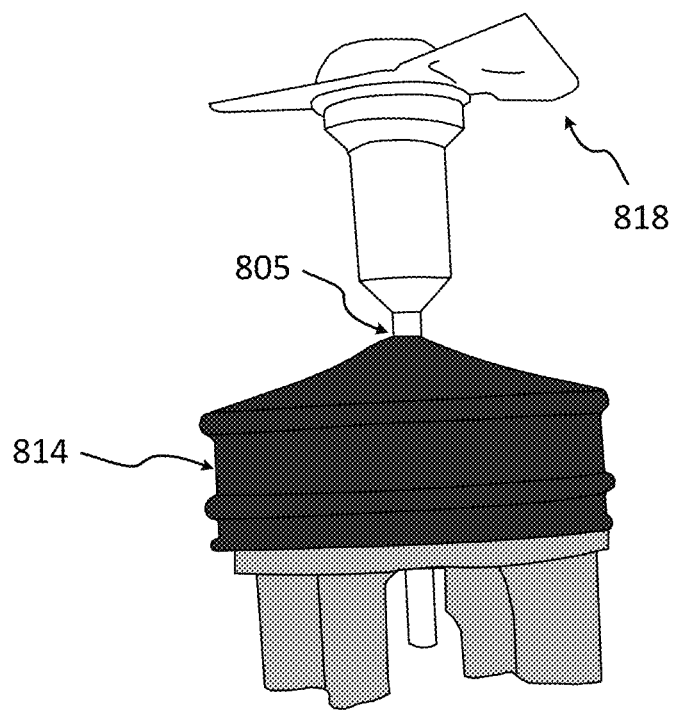
FIG. 8C illustrates an exemplary plunger with an integrated mixing vane.
Figure 8D:
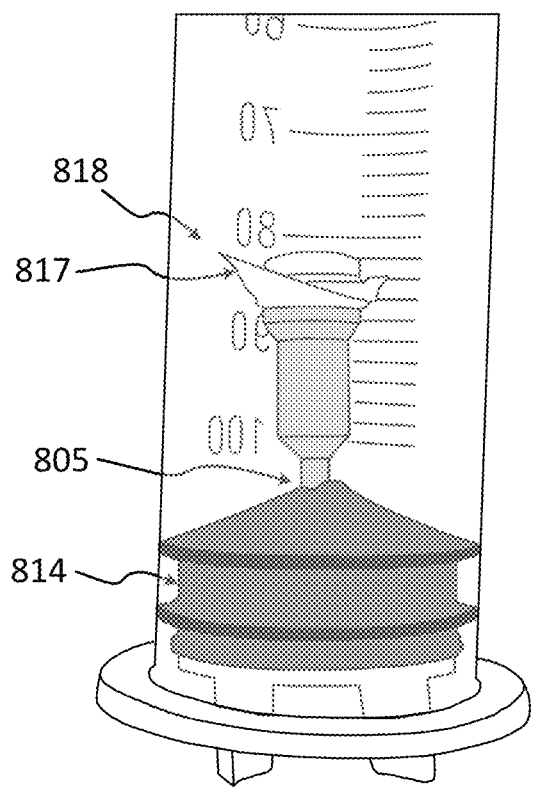
FIG. 8D illustrates the exemplary plunger with integrated mixing vane of FIG. 8C, disposed in a syringe.

In some implementations, only a portion of the plunger structure rotates. For example, as shown in FIG. 8C, a mixing vane 818 may be mounted at the tip of a plunger 814 (e.g., with a cylindrical mounting 805). FIG. 8D depicts the plunger with the mixing vane 818 in a syringe.

In some implementations, the mixing vane 818 rotates on its own as the plunger 814 is depressed within the syringe. In other implementations, the mixing vane 818 may be powered. For example, a small motor and power sources may be disposed within the plunger body, and the motor may be actuated automatically by a controller when movement of the plunger 814 is detected (e.g., by a switch, a proximity sensor, a piezoelectric element or by back electromagnetic force generated at the motor when the mixing vane 818 begins to rotate). As another example, the mixing vane 818 may be user-powered. For example, a hand crank may be coupled to the mixing vane 818 and extended out of the syringe (e.g., along the plunger handle) to permit mixing and agitation by a human user. In some implementations, gearing may be provided to increase rotational speed of the mixing vane 818 relative to rotational speed of any such hand crank.

Whether powered or unpowered, the mixing vane 818 may create turbulence or cavitation that creates microbubbles in the solution within the syringe as the plunger 814 is depressed. In addition to creating such microbubbles, the action of the mixing vane 818 may operate to mechanically break up larger bubbles into smaller ones.

As shown, the mixing vane 818 includes two opposing angled blades (e.g., angled relative to a plane of rotation). In other implementations, more blades may be provided, the angles may be adjusted, leading edges may be sharpened or notched, the blades may be perforated, and other configurations may be made to maximize the cavitation or turbulence created.

Figure 9A:
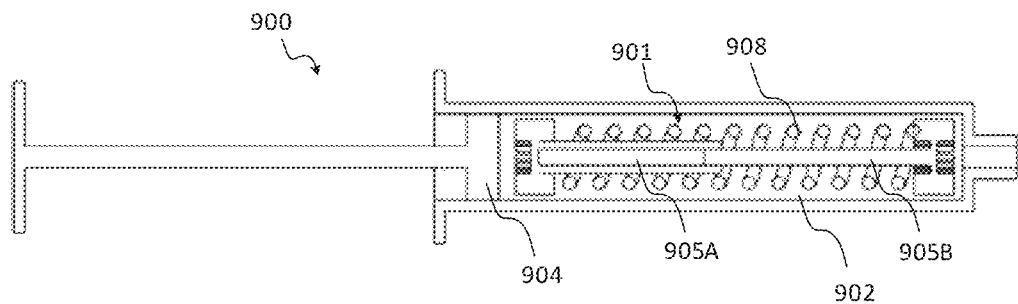
FIGS. 9A and 9B are cutaway views of an exemplary syringe with spring-loaded mixing vanes.
Figure 9B:
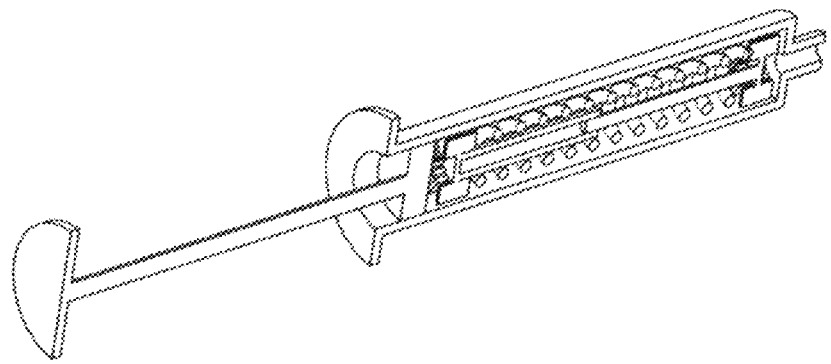
Figure 9C:
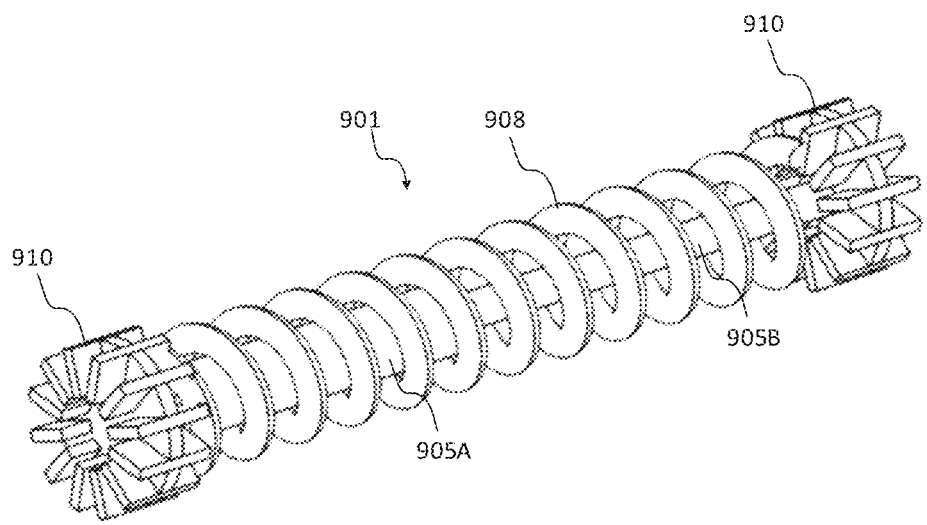
FIG. 9C is a perspective view showing additional detail of exemplary spring-loaded missing vanes.

As shown in FIG. 9A, FIG. 9B and FIG. 9C, a device residing in the interior volume 902 of a syringe 900 may have two parts 905A and 905B with an intermediate spring element 908 that is rotationally wound against each 905A and 905B other and locked in this state. The locking mechanism could be a keyway or shear pin feature (not shown) between the bodies 904A and 904B that is released by an axial motion of the plunger or by a magnet force applied or released from outside the syringe 900. The release of the locking mechanism may cause the wound spring energy to rotate the bodies 905A and 905B relative to each other. Vanes 910 or other mixing features on the body cause mixing of an air/fluid mixture in the syringe forming microbubbles that can then be injected via depression of the plunger mechanism 904.

Figure 10:
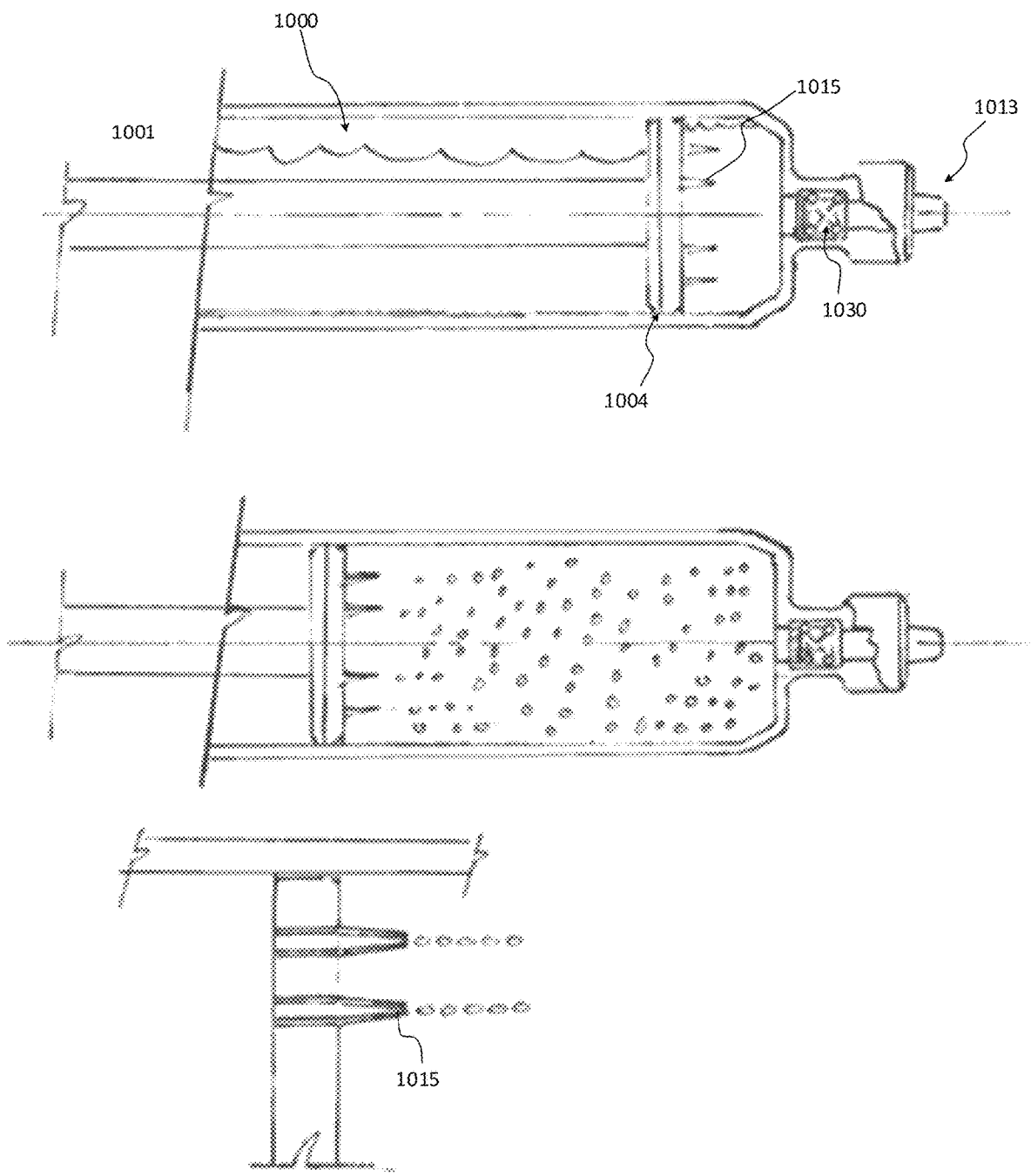
FIG. 10 provides cutaway views of an exemplary syringe with conical nozzles on the plunger.

In one implementation, as depicted in FIG. 10, a syringe 1000 includes a sealed proximal end 1001 and a check valve 1030 on the distal luer end 1013, and a plunger assembly fitted with conical nozzles. The syringe body FIG. 10 has the plunger 1004 extended and the syringe 1000 filled partly with liquid and partly with gas. The ratio can vary to determine gas-to-liquid ratio. Conical nozzles 1015 can be tapered to a defined aperture facilitating microbubble size. As shown, there is a plurality of nozzles 1015 on the plunger.

In some implementations, the syringe 1000 comes pre-filled with a ratio of liquid and gas. The user draws the plunger 1004 towards the proximal end 1001 and as the gas compresses and fluid mixes and passes through the nozzles 1015, the gas and fluid are compressed into the inside bore of the nozzles. As the gas and fluid escape into the distal portion of the syringe 1000, the lower pressure side of the syringe the gas microbubbles expand and are dispersed through the fluid, exhibited. The aperture of the nozzles 1015 may control the size of the microbubbles.

Figure 11:
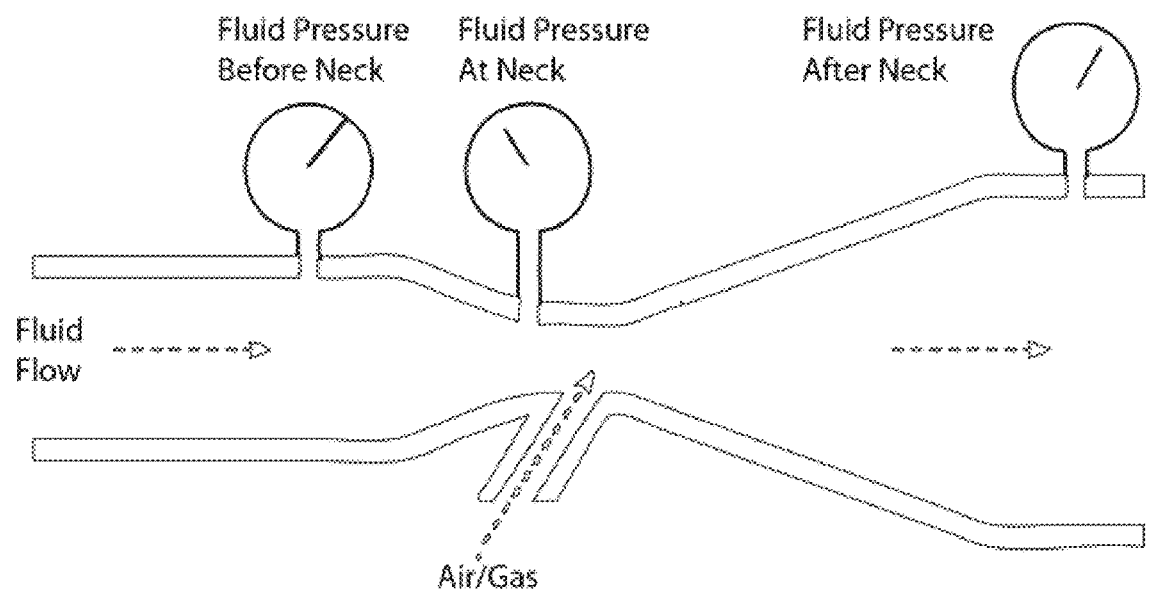
FIG. 11 illustrates a venturi implementation.

In some implementations, as depicted in FIG. 11, a portion of the fluid path between the syringe and the patient comprises a section that converges to a smaller diameter "neck" region and then diverges back to a larger diameter fluid path (a "venturi" implementation). The smaller diameter neck region causes fluid velocity to increase and fluid pressure to decrease. Small inlet ports or holes in the low pressure necked region allow air or supplied gases to enter the fluid stream and mix as microbubbles into the fluid through a process known as air entrainment in some industries. Additionally, a spring-loaded syringe driver (not shown) or motion system can provide a controlled fluid volume per unit time in a specific range to ensure correct fluid velocities for the design are met to maximize air entrainment. In some implementations, air may be drawn in at the neck region; in other implementations, a different gas, such as carbon dioxide or nitrogen may be provided.

Additional implementations can include screens, plates or mesh (either perforated or woven) to create turbulence between the fluid and gas. Screens can be aligned in a way to predict the microbubble size and amount. Screens, plates or mesh may be made of metals, plastics or polymers. A foam filter may be disposed downstream from screen, plate, or mesh elements (e.g., to filter out larger bubbles). In some implementations, a microplane structure may be employed (e.g., several layers of material "laminated" together but with enough space between to create turbulence and microbubbles). In some implementations, additional structures may be employed to regulate the forward progress of the plunger within a syringe. For example, whereas some syringes may have a smooth interior, others may include ridges to slow the forward movement of the plunger at particular points (e.g., to create additional turbulence).

Figure 12:
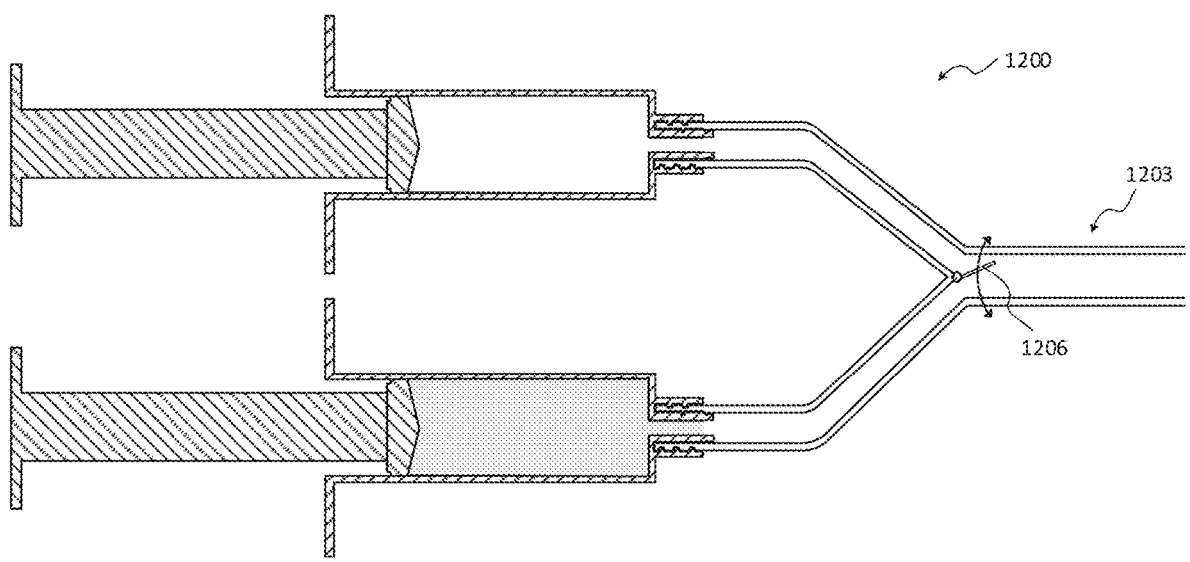
FIG. 12 illustrates an exemplary side-by-side mixing syringe.

Side-by-side or to chamber mixing systems may also be possible. In some implementations, one of which is depicted in FIG. 12, metered air and saline may be pushed from a two-chamber syringe 1200 through a mixing tip 1203 that provides an oscillating valve 1206 which provides agitation by the valve swinging between side-by-side gas and fluid chambers. In other implementations, the oscillating valve 1206 may be replaced with a tortuous path that creates turbulence and introduces microbubbles. In other implementations, a spinning plunger version or plungers providing agitation using the hydraulic energy of reciprocating the syringe back and forth, and various other means to pull air into the fluid reservoir such as via a venturi in communication to ambient air.

Figure 13A:
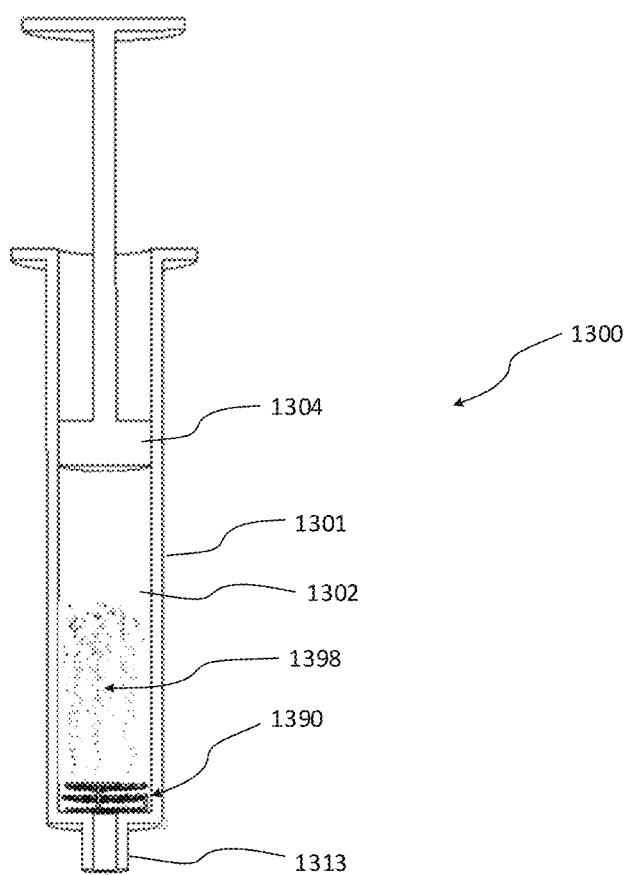
FIG. 13A illustrates an exemplary syringe in which microbubbles can be generated through electrolysis.
Figure 13B:
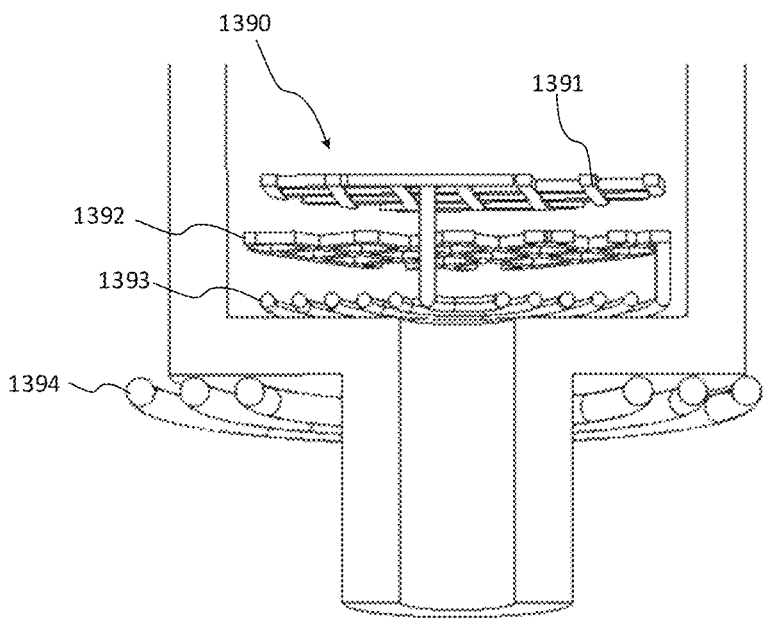
FIG. 13B illustrates additional details of the syringe shown in FIG. 13A.

An electrolysis implementation is illustrated in FIG. 13A and FIG. 13B. In the implementation shown, a syringe 1300 includes electrodes 1390 near the distal tip 1313, in fluid contact with the liquid 1302 inside the syringe 1300. When the electrodes 1390 are energized, microbubbles 1398 may be formed.

The electrodes 1390 may include an anode electrode 1391 and a cathode electrode 1392. The anode electrode 1391 and cathode electrode 1392 may be in the form of plates, screens, wires or as thin deposited films, and they may comprise a stable material that will not erode during electrolysis in a solution such as saline or other intravenous fluid. The specific design of the electrodes 1391 and 1392 may influence bubble size. For example, in some implementations, very fine screens or grids may produce smaller microbubbles, relative to coarser screens or larger grids. Additionally, the electrode surfaces may have a fine or rough texture to encourage gas microbubble formation in discrete locations on the electrode surface.

To energize the electrodes 1391 and 1392, an internal power coil 1393 may be disposed inside the barrel 1301 of the syringe 1300, and an external power transmitting coil 1394 may be disposed on the exterior of the syringe 1300, near the internal power coil 1393. In some implementations, in operation, an alternating current is applied to the external power transmitting coil 1394 to induce a current on the internal power coil 1393, thereby energizing the anode electrode 1391 and cathode electrode 1392 and creating microbubbles.

The magnitude of the induced current and/or voltage may also influence bubble size, in addition to the specific design of the electrodes 1391 and 1392. A "settling time" may facilitate separation of different size microbubbles. For example, larger bubbles may rise to the top of a vertically oriented syringe 1300; and if there is some air near the plunger 1304, these large bubbles may escape the liquid, whereas smaller microbubbles may remain in solution. In implementations in which this is the case, a prescribed settling time may enable a user to further control bubble size.

In some implementations, the syringe 1300 is filled with liquid (e.g., saline), and energy is applied to the external power transmitting coil 1394 to form microbubbles, as described above. Power may be removed from the external power transmitting coil 1394. And the syringe may be used to deliver aerated liquid, via intravenous tubing (not shown) to a patient undergoing a contrast study.

Figure 6B:
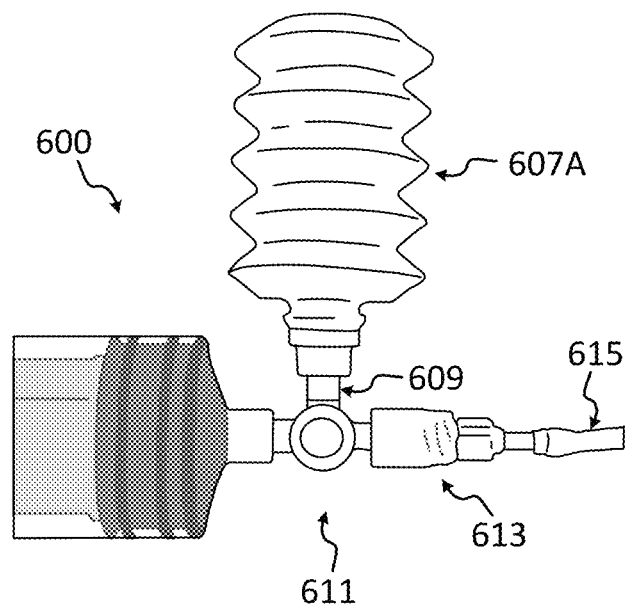
FIG. 6B is a perspective view of an exemplary shuttle valve mixing syringe.

While several implementations have been described with reference to exemplary aspects, it will be understood by those skilled in the art that various changes may be made and equivalents may be substituted for elements thereof without departing from the contemplated scope. For example, implementations in which mechanisms for producing microbubbles are disposed interior to a syringe may, in other implementations, be disposed exterior to the syringe. More specifically, for example, the check valve assembly 350 illustrated in and described with reference to FIGS. 3A, 3B and 3C could be disposed outside of the syringe 300, in another device that is in fluid connection with the syringe 300; similarly, the microfluidic discs 444 illustrated in and described with reference to FIGS. 4A, 4B and 4C could be disposed outside of the syringe 400, in a device that is in fluid connection with the syringe 400; the exchange chamber 607/shuttle valve 609/diverter valve 611 of FIG. 6 is shown integral to the syringe 600, but these elements 607, 609 and 611 could also be separate from and external to the syringe 600; the cartridge 713 of FIG. 7 is shown inside the syringe, but it could be disposed outside the syringe, in a device that is in fluid connection with the syringe; the conical nozzles 1015 shown as integral with the plunger 1004 in FIG. 10 may also be disposed external to the syringe 1000—for example, in a separate device that is in fluid communication with the syringe 1000, through which liquid may be drawn into the syringe, and which may be preloaded with some liquid and some air. In other implementations, various components may be disposed inside or outside of a syringe.

In some implementations, the mechanical components of a syringe (e.g., a barrel and a plunger) may be reproduced in another form that provides a similar function. For example, rotating cams or fingers/tubing (e.g., as employed in in infusion pumps), may be deployed in conjunction with aspects described herein to create microbubbles in devices having form factors other than syringes.

Many other variations are possible, and modifications may be made to adapt a particular situation or material to the teachings provided herein without departing from the essential scope thereof. Therefore, it is intended that the scope include all aspects falling within the scope of the appended claims.

What is claimed is:

1. A method for generating microbubbles, the method comprising:
   providing a syringe comprising a barrel defining an interior volume, a plunger, a tip and a check valve assembly; the check valve assembly comprising: (i) one or more inlet ports; (ii) a check valve that is configured to open when the plunger is drawn back by a user; (iii) one or more nozzles in fluid communication with the interior volume and, when the check valve is open, in fluid communication with the one or more inlet ports;
   drawing back the plunger with the tip coupled to a source of liquid to thereby draw the liquid into the interior volume;
   removing a seal from the one or more inlet ports, decoupling the tip from the source of liquid, and sealing the tip;
   further drawing back the plunger to draw gas adjacent the inlet ports into the interior volume to form microbubbles in the liquid already drawn into the interior volume;
   unsealing the tip and coupling the tip to an intravenous line associated with a patient undergoing a bubble study;
   depressing the plunger to force the liquid and the formed microbubbles into the intravenous line.

2. The method of claim 1, wherein the one or more nozzles are configured to form, in a liquid that is in the interior volume, microbubbles having a diameter that corresponds to a diameter of at least one of the one or more nozzles, when the plunger is drawn back.

3. The method of claim 1, wherein the check value comprises a flexible membrane that is configured to open towards the interior volume.

4. The method of claim 2, wherein the one or more nozzles are configured to have diameters that are a fraction of a diameter of a desired microbubble.

5. The method of claim 4, wherein the one or more nozzles have diameters that are selected from 500 angstroms, 1 micron, 2 microns, 3 microns and 4 microns.

6. The method of claim 3, wherein the check valve comprises rubber or silicone.

* * * * *